United States Patent
Russak

(10) Patent No.: US 10,782,310 B2
(45) Date of Patent: Sep. 22, 2020

(54) SAMPLE MIXING CONTROL

(71) Applicant: AZURE VAULT LTD., Ramat-Gan (IL)

(72) Inventor: Ze'ev Russak, Netanya (IL)

(73) Assignee: AZURE VAULT LTD., Ramat-Gan (IL)

( * ) Notice: Subject to any disclaimer, the term of this patent is extended or adjusted under 35 U.S.C. 154(b) by 0 days.

(21) Appl. No.: 16/086,303

(22) PCT Filed: Jun. 10, 2016

(86) PCT No.: PCT/IB2016/053423
§ 371 (c)(1),
(2) Date: Sep. 18, 2018

(87) PCT Pub. No.: WO2017/163112
PCT Pub. Date: Sep. 28, 2017

(65) Prior Publication Data
US 2019/0101556 A1    Apr. 4, 2019

Related U.S. Application Data

(60) Provisional application No. 62/310,844, filed on Mar. 21, 2016.

(51) Int. Cl.
*G16B 40/00* (2019.01)
*C12Q 3/00* (2006.01)
(Continued)

(52) U.S. Cl.
CPC ......... *G01N 35/00732* (2013.01); *B01D 3/00* (2013.01); *B01D 3/42* (2013.01);
(Continued)

(58) Field of Classification Search
None
See application file for complete search history.

(56) References Cited

U.S. PATENT DOCUMENTS

| 5,671,153 A | 9/1997 | Brinkmeyer et al. |
| 2011/0177592 A1 | 7/2011 | Faustman et al. |

(Continued)

OTHER PUBLICATIONS

International Search Report dated Sep. 16, 2016 in PCT/IB2016/053423 (3 pages).

(Continued)

*Primary Examiner* — Neil N Turk
(74) *Attorney, Agent, or Firm* — Acuity Law Group, PC; Michael A. Whittaker

(57) ABSTRACT

A method for controlling the mixing of a plurality of samples subject to a chemical process, the method comprising computer executed steps, the steps comprising: for each one of the samples, receiving respective data on a result obtained for the sample using the chemical process, and for each one of at least two of the samples, further receiving respective data on classification of the sample into one of at least two classes, for each one of the samples, calculating a respective rank based on the result obtained for the sample using the chemical process, finding among the samples, at least one pair of samples classified into different ones of the classes, such that for each respective one of the found pairs, none of the samples having a calculated rank in between the ranks calculated for the two samples of the found pair are classified into one of the classes.

19 Claims, 11 Drawing Sheets

(51) Int. Cl.
*G05B 15/00* (2006.01)
*C12M 1/36* (2006.01)
*G01N 35/00* (2006.01)
*C12Q 1/68* (2018.01)
*B01D 3/42* (2006.01)
*B01D 3/00* (2006.01)
*B01J 4/00* (2006.01)
*B01L 7/00* (2006.01)
*G01N 30/88* (2006.01)
*G16C 20/10* (2019.01)
*G16C 20/70* (2019.01)
*G01N 33/569* (2006.01)

(52) U.S. Cl.
CPC . *B01J 4/00* (2013.01); *B01L 7/00* (2013.01); *C12M 1/36* (2013.01); *C12Q 1/68* (2013.01); *C12Q 3/00* (2013.01); *G01N 35/00* (2013.01); *G01N 35/00613* (2013.01); *G05B 15/00* (2013.01); *G16B 40/00* (2019.02); *G01N 33/56988* (2013.01); *G01N 2030/8804* (2013.01); *G01N 2035/0096* (2013.01); *G01N 2035/00465* (2013.01); *G01N 2035/00841* (2013.01); *G01N 2800/26* (2013.01); *G16C 20/10* (2019.02); *G16C 20/70* (2019.02)

(56) References Cited

U.S. PATENT DOCUMENTS

| | | |
|---|---|---|
| 2011/0179044 A1 | 7/2011 | Crum et al. |
| 2012/0166100 A1 | 6/2012 | Russak |
| 2012/0239309 A1 | 9/2012 | Russak |
| 2015/0100242 A1 | 4/2015 | Zeng et al. |
| 2015/0127271 A1 | 5/2015 | Liu et al. |
| 2015/0234779 A1 | 8/2015 | Raghunathan et al. |

OTHER PUBLICATIONS

Written Opinion dated Sep. 16, 2016 in PCT/IB2016/053423 (9 pages).
International Preliminary Report on Patentability dated Feb. 16, 2018 in PCT/IB2016/053423 (5 pages).
Notice of Allowance issued by the Canadian IP Office dated Jul. 18, 2018 on CA 3,008,989.

```
┌─────────────────────────────────────────────┐
│ Obtain one Zika virus Positive specimen and one Zika │ 710
│         virus Negative specimen             │
└─────────────────────────────────────────────┘
                      │
                      ▼
┌─────────────────────────────────────────────┐
│              Preform calibration            │ 720
└─────────────────────────────────────────────┘
                      │
                      ▼
┌─────────────────────────────────────────────┐
│           Zika virus qPCR classifier        │ 730
└─────────────────────────────────────────────┘
```

Fig. 7

810 — Obtain one Zika virus Positive specimen and one Zika virus Negative specimen 820 — Prepare dilution series by diluting the positive specimen using the negative specimen 830 — Project the qPCR curves on the fiddler vectors 840 — Search for the boundaries within the fiddler vector between the positive and negative qPCR curves 850 — Meet criteria?
- No → 860 — Synthesize missing data → (back to 840)
- Yes ↓

870 — Define the classifier parameters.

Fig. 8

SAMPLE MIXING CONTROL

CROSS-REFERENCE TO RELATED APPLICATIONS

The present invention is filed under 35 U.S.C. § 371 as the United States national phase of International Application No. PCT/IB2016/053423, filed Jun. 10, 2016, which designated the United States, and which claims priority to U.S. Provisional Application No. 62/310,844, filed Mar. 21, 2016, each of which is hereby incorporated in its entirety including all tables, figures, and claims.

FIELD AND BACKGROUND OF THE INVENTION

The present invention relates to automation of laboratories, and more particularly, but not exclusively to a method and an apparatus for controlling the mixing of samples subject to a chemical process such as PCR (Polymerase Chain Reaction), an HPLC (High Performance Liquid Chromatography) process, etc.

In recent years, advanced laboratory automation has often been the result of new challenges that laboratories—especially laboratories engaged in testing large numbers of samples for the presence of viruses such as HIV (Human Immunodeficiency Virus) or the Hepatitis-C Virus—are often faced with.

Indeed, laboratory automation and the growing emergence of laboratory machines (say robotics) have transformed the typical workday for many scientists and laboratory technicians in those laboratories.

For example, liquid handling robots, say robots that dispense selected quantities of physical samples (say blood samples, saliva samples, etc.) to a designated container, or similar machines are very often used in automation of laboratories.

In one example, a simple laboratory robot may simply dispense an allotted volume of a liquid (say a blood sample) from a motorized pipette or syringe.

More sophisticated robots may also manipulate the position of the dispensers and containers and/or integrate additional laboratory devices, such as centrifuges, micro plate readers, heat sealers, heater, shakers, bar code readers, photometric devices, storage devices, incubators, etc.

Some robots may also perform multiple operations such as sample transport, sample mixing, manipulation and incubation, transporting vessels between workstations, etc.

Subsequently to one or more of the above mentioned operations, the samples may undergo a chemical process—say in a PCR machine, an HPLC instrument, etc., as known in the art. Then, in a separate and final step, a classification model developed beforehand is used to classify each of the samples, say for diagnosing the person from whom one of the samples is originally obtained, as HIV Positive, HIV Negative, etc.

SUMMARY OF THE INVENTION

According to one aspect of the present invention, there is provided a method for controlling the mixing of a plurality of samples subject to a chemical process, the method comprising computer executed steps, the steps comprising: a) for each one of the samples, receiving respective data on a result obtained for the sample using the chemical process, and for each one of at least two of the samples, further receiving respective data on classification of the sample into one of at least two classes, b) for each one of the samples, calculating a respective rank based on the result obtained for the sample using the chemical process, c) finding among the samples, at least one pair of samples classified into different ones of the classes, such that for each respective one of the found pairs, none of the samples having a calculated rank in between the ranks calculated for the two samples of the found pair are classified into one of the classes, d) identifying a pair consisting of samples that are least close to each other in their calculated ranks among the found pairs, and e) provided none of the samples have a calculated rank in between the ranks calculated for the samples of the identified pair, generating instructions for mixing at least one pair of samples qualitatively identical to the identified pair, to yield a respective new sample.

According to a second aspect of the present invention, there is provided an apparatus for controlling the mixing of a plurality of samples subject to a chemical process, comprising: a computer processor, a data receiver, implemented on the computer processor, configured to receive for each one of the samples, respective data on a result obtained for the sample using the chemical process, and for each one of at least two of the samples, to further receive respective data on classification of the sample into one of at least two classes, a rank calculator, in communication with the data receiver, configured to calculate for each one of the samples, a respective rank based at least on the result obtained for the sample using the chemical process, a pair finder, in communication with the rank calculator, configured to find among the samples, at least one pair of samples classified into different ones of the classes, such that for each respective one of the found pairs, none of the samples having a calculated rank in between the ranks calculated for the two samples of the found pair are classified into one of the classes, a least close pair identifier, in communication with the pair finder, configured to identify a pair consisting of samples that are least close to each other in their calculated ranks among the found pairs, and an instruction generator, in communication with the least close pair identifier, configured to generate instructions for mixing at least one pair of samples qualitatively identical to the identified pair, to yield a respective new sample, provided none of the samples have a calculated rank in between the ranks calculated for the identified pair.

According to a third aspect of the present invention, there is provided a non-transitory computer readable medium storing computer processor executable instructions for performing steps of controlling the mixing of a plurality of samples subject to a chemical process, the steps comprising: a) for each one of the samples, receiving respective data on a result obtained for the sample using the chemical process, and for each one of at least two of the samples, further receiving respective data on classification of the sample into one of at least two classes, b) for each one of the samples, calculating a respective rank based on the result obtained for the sample using the chemical process, c) finding among the samples, at least one pair of samples classified into different ones of the classes, such that for each respective one of the found pairs, none of the samples having a calculated rank in between the ranks calculated for the two samples of the found pair are classified into one of the classes, d) identifying a pair consisting of samples that are least close to each other in their calculated ranks among the found pairs, and e) provided none of the samples have a calculated rank in between the ranks calculated for the samples of the identified pair, generating instructions for mixing at least one pair of samples qualitatively identical to the identified pair, to yield a respective new sample.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. The description taken with the drawings making apparent to those skilled in the art how the several forms of the invention may be embodied in practice.

In the drawings:

FIG. 7 is a first flowchart schematically illustrating an exemplary scenario of controlling the mixing of a plurality of samples subject to a chemical process, according to an exemplary embodiment of the present invention.

FIG. 8 is a second flowchart schematically illustrating the exemplary scenario of controlling the mixing of a plurality of samples subject to a chemical process, according to an exemplary embodiment of the present invention.

DESCRIPTION OF THE PREFERRED EMBODIMENTS

Figure 1:
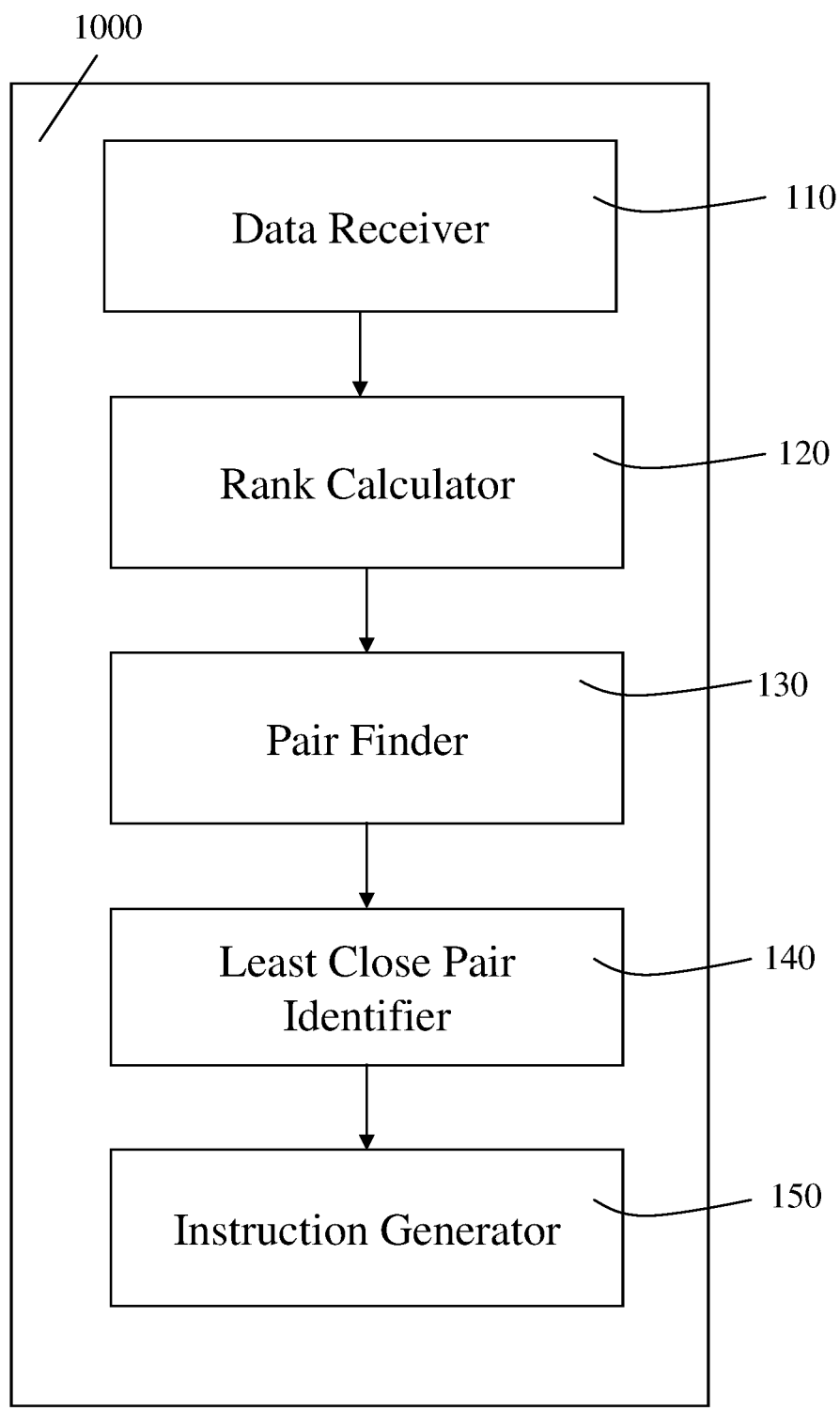
FIG. 1 is a block diagram schematically illustrating a first exemplary apparatus for controlling the mixing of a plurality of samples subject to a chemical process, according to an exemplary embodiment of the present invention.

The present embodiments comprise an apparatus and a method of controlling the mixing of a plurality of samples subject to a chemical process.

Laboratory automation and the growing emergence of laboratory robotics have transformed the typical workday for many scientists and laboratory technicians in nowadays laboratories.

For example, machines such as liquid handling robots are very often used in automation of laboratories—say robots that dispense selected quantities of samples to a container or perform multiple operations such as sample mixing, and manipulation.

Usually, subsequently to one or more of the above mentioned operations, the samples handled by such laboratories undergo a chemical process—say in a PCR or an HPLC machine.

Then, in a separate and final step, a classification model developed beforehand is used to classify each of the samples, say for diagnosing each person from whom a respective one of the samples is originally obtained, as HIV Positive, HIV Negative, etc.

Classification models of the sort used in diagnosis need to be developed based on many (say hundreds and even thousands) test samples of known in advance classification (say a classification based on clinical examination of the patients from whom the many samples are originally obtained).

The development of a classification model is thus a process that may take a long period of time and require extensive resources (say medical examinations of the patients by physicians, examinations of reaction curves obtained from the samples by experts, etc).

Further, the classification models may need to be verified and validated according to strict criteria defined by government agencies or intergovernmental agencies such as the FDA (Food and Drug Administration), WHO (World health organization), etc.

However, in some cases, such a classification model may be unavailable yet (say because no classification model has been developed yet or because validation and verification processes required for FDA Approval of the model have not been finalized yet).

For example, in an early stage of a rapid outbreak of a new disease or of a new strand of a life threatening virus—such as the Zika Virus outbreak of 2015—such a classification model may be unavailable yet.

In the early stage, a laboratory team would typically receive many hundreds and even thousands of samples (say blood samples) obtained from people who live in an area in which the outbreak occurs. However, in the early stage, only a small number of the samples belong to people already diagnosed with the new disease or virus strand.

Under such circumstances, the laboratory team may need to develop a classification model themselves.

However, with hitherto used methods, the laboratory team would not be able to develop such a classification model before a large enough number of the samples are already classified.

In one example, the already classified samples are samples taken from people that already show clear symptoms of the disease and can thus be diagnosed with the disease.

In a second example, the samples are samples classified by experts say according to reaction curves that represent the progress of a chemical reaction such as PCR (Polymerase Chain Reaction), as described in further detail hereinbelow.

Thus, with the hitherto used methods, the development of the classification model is likely to take many weeks or even months. Meanwhile, the disease may spread into wider areas and claim the lives of more and more victims.

Potentially, according to an exemplary embodiment of the present invention, machines (say robots) in use for mixing samples in a laboratory may be controlled according to instructions that are generated, so as to arrive at a classification model faster and based on a classification of a smaller number of samples.

According to an exemplary embodiment of the present invention, in a method for controlling the mixing of a plurality of samples, each one of the samples is subject to a chemical process (PCR, HPLC, etc.).

Subsequently, in the exemplary method, for each one of the samples, there is received respective data on a result obtained for the sample using the chemical process.

In one example, the data on the result includes physical parameter values such as fluorescence values, etc., as measured over a chemical apparatus in which the sample is subject to a PCR Process, during the PCR Process, and a respective time of measurement of each specific one of the values.

Further, for each one of at least two of the samples, there is further received data on classification of the respective sample into one of at least two classes (say as Negative or as Positive), as described in further detail hereinbelow.

In one example, a few of the samples are received with data on a classification of the few samples according to clinical symptoms.

In the example, each one of the few classified samples is received with data on classification of the sample as positive or rather as negative, based on clinical symptoms expressed by a specific person (i.e. patient) from whom the sample is obtained.

In a second example, a few of the samples are received with data on a classification of the few samples according to examination of sample results by Experts.

In the example, each one of the few classified samples is received with data on classification of the sample as positive or rather as negative based on examination of the data on the results by Experts, say by PCR Experts who examine reaction curves that depict the results, as known in the art.

Optionally, one of the classes is simply a class of samples that could not be classified into any one of the other classes, which class may also be referred to as a class of Ambiguous Samples.

Thus, in one example, a class of Ambiguous Samples includes samples obtained from persons who appear sick but have clinical symptoms characteristic of different diseases, and therefore cannot be categorically classified as Positive or Negative with respect to a specific disease based on their clinical symptoms alone.

In a second example, a class of Ambiguous Samples includes samples that the results received for are too marginal for the Experts to determine whether the samples are positive or negative.

The remaining samples are not classified yet—say because the remaining samples belong to people who live in the geographical area in which the new disease erupts, but do not express clinical symptoms yet or because no time is left for the Experts to classify the remaining samples.

In the exemplary method, for each one of the samples, there is calculated a respective rank based at least on the result obtained for the sample using the chemical process, as described in further detail hereinbelow.

Then, there is found among the samples one or more pairs of samples that are classified into different ones of the classes, such that for each respective one of the found pairs, none of the samples that have a calculated rank in between the ranks calculated for the two samples of the found pair are classified into any of the classes.

That is to say that each of the found pairs defines a gap among the ranks calculated for the samples—i.e. a region of uncertainty as to a location of a borderline that separates between classes in terms of rank values, and thus a gap in a classification model evolving based on the results obtained for the samples, through the steps of the method.

Next, there is identified a pair that consists of samples that are least close to each other in their calculated ranks among the found pairs, thus identifying the widest gap in the evolving model, as described in further detail hereinbelow.

Then, provided none of the samples for which the data is received have a calculated rank in between the ranks calculated for the identified pair, there are generated instructions for mixing at least one pair of samples qualitatively identical to the identified pair, to yield a respective new sample.

Thus, upon identifying the widest gap—namely, the one defined by that identified pair that consists of samples that are least close to each other in their calculated ranks among the found pairs—there are generated instructions for mixing one or more pairs of samples qualitatively identical to the identified pair.

The mixing is believed to yield a respective new sample that is likely to be calculated a rank in between the ranks of the two samples of the identified pair. The gap defined by the identified pair is thus likely to be divided into two smaller gaps.

Thus, with the present invention, a machine (say a laboratory robot) may be instructed to mix samples in a way which iteratively narrows down gaps in the evolving classification model.

The narrower are the gaps among the calculated ranks, the more accurate is a partition of the ranks' range of values into a plurality of ranges, each range corresponding to a respective class, and the more accurate the classification model becomes.

Thus, with embodiments of the present invention, rather than mixing samples according to instructions prescribed arbitrarily in advance to yield a final and planned in advance set of samples, a machine (say robot) may be instructed dynamically to mix samples according to instructions that are generated dynamically.

Potentially, the dynamic generation of the instructions allows a classification model to evolve more quickly, while relying on an in-advance classification of only a small number of the received samples (say according to the clinical symptoms expressed by fewer persons or according to examination of fewer results by the Experts).

With exemplary embodiments of the present invention, a mixing of samples (say by laboratory robots) is thus driven and controlled using instructions derived from an evolving classification method.

Consequently, the classification model is likely to be developed within a relatively short time period, using a significantly lower number of samples classified before having the fully developed classification model, as described in further detail hereinbelow.

Thus, potentially, with the exemplary embodiments of the present invention, a laboratory team may be able to cope more efficiently with a rapid outbreak of a new disease or life threatening virus strand, by developing a classification model using a much smaller number of clinical tests.

The principles and operation of an apparatus and s method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings.

The invention is capable of other embodiments or of being practiced or carried out in various ways. Also, it is to be understood that the phraseology and terminology employed herein is for the purpose of description and should not be regarded as limiting.

Reference is now made to FIG. 1, which is a block diagram schematically illustrating a first exemplary apparatus for controlling the mixing of a plurality of samples subject to a chemical process, according to an exemplary embodiment of the present invention.

Apparatus 1000 for controlling the mixing of a plurality of samples subject to a chemical process may be implemented using electric circuits, computer software, computer hardware, etc.

The apparatus 1000 may be implemented on a computer, say on a computer on a chip connectable to one or more machine(s) in use in a laboratory (say to a reaction apparatus such as a PCR Apparatus, to a laboratory robot used for mixing, etc.), which chip may be installed on the machine or be in communication therewith, etc.

Thus, in one example, the apparatus 1000 is implemented on a computer chip that is a part of a computerized controller (say a computerized controller used in a chemical laboratory)—say a controller which controls a robot used for mixing physical samples (say blood samples, saliva samples, etc.) in a laboratory of a central institution for monitoring the spread of infectious diseases.

The apparatus 1000 may thus include one or more computer processors.

The apparatus 1000 further includes one or more additional parts described in further detail hereinbelow, such as the classification obtainer or the parts denoted 110-150 in FIG. 1, as described in further detail hereinbelow.

The additional parts may be implemented as software—say by programming the one or more computer processors to execute the method described in further detail and illustrated using FIG. 4 hereinbelow, as hardware—say as an electric circuit that implements at least a part of the method, etc., or any combination thereof.

The apparatus 1000 includes a data receiver 110.

The data receiver 110 receives data on a result obtained for each respective one of two or more physical samples (say blood samples, saliva samples, urine samples, etc.) using a chemical reaction that the sample is subjected to, as described in further detail hereinbelow.

The result may be obtained, for example, using a chemical process such as a PCR (Polymerase Chain Reaction) Process or a HPLC (High Performance Liquid Chromatography) process, as described in further detail hereinbelow.

Thus, in a first example, the data received by the data receiver 110 is data on a result that includes physical parameter values say fluorescence intensity values, measured over a reaction apparatus in which the sample is subject to a PCR Process, during the PCR Process.

In the first example, the data receiver 110 further receives in the data, a respective time of measurement of each one of the fluorescence intensity values, or a temperature measured in the reaction apparatus in which the PCR process takes place when each respective one of the fluorescence intensity values is measured.

In a second example, the chemical process is a HPLC (High Performance Liquid Chromatography) process. In the example, a chemical process apparatus in use is a HPLC instrument which includes a sampler, a pump, one or more detectors, and a microprocessor. The detectors may include, but are not limited to a UV-Vis Absorbance Detector, a Chromatography Detector, etc., as known in the art.

The sampler brings the sample into a mobile phase stream which carries the sample into an analytical column, as known in the art, and the pump delivers the desired flow and composition of the mobile phase through the analytical column.

In the example, each detector generates a signal proportional to the amount of a specific component or a specific component type present in the sample when the sample emerges from the analytical column, as known in the art.

In the example, the signals generated by the detectors are processed by the HPLC instrument's microprocessor, to yield the data on the result for the sample.

Then, the data on the result for the sample is communicated from the HPLC Instrument (say over a Local Area Network or a Wide Area network—as known in the art), and is received by the data receiver 110, as described in further detail hereinbelow.

For each one of at least two of the samples, the data receiver 110 further receives data on classification of the sample into one of at least two classes (say as Negative or as Positive), as described in further detail hereinbelow.

Thus, in a first example, a few of the samples are classified according to clinical symptoms. In the example, for each one of the few classified sample, the data receiver 110 receives data on classification of the sample as positive or rather as negative, based on clinical symptoms expressed by a specific person from whom the sample is obtained.

In a second example, the few samples are rather samples classified beforehand (i.e. prior to receipt of the data by the data receiver 110) by an expert through manual examination of the results obtained for each specific one of the few sample, as described in further detail hereinbelow.

For example, a PCR Expert may classify the sample based on a curve that depicts the course of a PCR process that the sample is subject to, as measured fluorescence values per time or cycle of the PCR process, as known in the art. The values per time or cycle thus form the result for the sample.

Similarly, a HPLC Expert may classify the sample based on the result obtained for the sample based on a HPLC process carried out using a HPLC Instrument, as described in further detail hereinbelow.

Optionally, one of the classes is simply a class of samples found to be non-classifiable into any one of the remaining classes, which class may also be referred to as a class of Ambiguous Samples.

Thus, in one example, a class of Ambiguous Samples includes samples obtained from persons who appear sick but have clinical symptoms characteristic of different diseases. Consequently, the samples cannot be categorically classified beforehand (i.e. prior to receipt of the data) as Positive or Negative with respect to a specific disease based on their clinical symptoms alone.

In a second example, the class of Ambiguous Samples includes samples that a PCR or a HPLC Expert hired to classify some of the samples beforehand, tries to classify but finds to be ambiguous.

The remaining samples are samples that are not classified yet, say because the remaining samples belong to people who do not express clinical symptoms yet or because the number of samples is too high for a PCR or HPLC Export to classify within a time available or budgeted for.

Indeed, for example, during an outbreak of a life threatening disease such as Ebola, many hundreds or even thousands of samples (especially positive ones which are by definition, less common) may need to be taken from people who live in a wide geographical area over which the disease appears to spread rapidly.

During such an outbreak, the hundreds or thousands of samples may need to be used to develop a classification mode quickly, while most of the people from whom the samples are taken do not express any clinical symptom typical of the disease yet. However, the samples taken from the people who do not express any clinical symptom typical of the disease cannot be classified yet.

The apparatus 1000 further includes a rank calculator 120, in communication with the data receiver 110.

For each one of the samples for which the data receiver 110 receives the respective data on the result obtained for the sample, the rank calculator 120 calculates a respective rank.

The rank calculator 120 calculates the rank based at least on the result obtained for the sample using the chemical process, according to a predefined formula, rule, parameter, etc., as described in further detail hereinbelow. The formula, rule, parameter may be defined in advance, say by an operator, administrator, or programmer of apparatus 1000.

In one example, the rank calculator 120 identifies in the received results, a most significant parameter or a combination of most significant parameters, and calculates the rank based on the identified most significant parameter or combination, as described in further detail hereinbelow.

The most significant parameter may be, for example, a parameter that shows a maximal variance, or a parameter that is very often relied on for classifying samples using a chemical reaction of the type used to obtain the results—say a Threshold Cycle (Ct) Value for PCR, etc., as known in the art.

Thus, in a first example, the rank calculator 120 calculates the rank based on a Fiedler Vector that the rank calculator 120 derives based on an analysis of the results received by the data receiver 110, say as the value of the Fiedler Vector as calculated for the sample, as described in further detail hereinbelow.

In a second example, the rank calculator 120 calculates the rank based on a discriminating function that the rank calculator 120 calculates through an SVM (Support Vector Machine) based analysis of the results received by the data receiver 110, as described in further detail hereinbelow.

In a third example, the respective data received by the data receiver 110 on each sample's result is made of fluorescence values measured during a PCR Process that the sample is subject to. The received data further includes a respective time of measurement of each respective one of the values, or a respective number of the cycle at which the value is measured, as described in further detail hereinbelow.

In the third example, for calculating the rank, the rank calculator 120 identifies a PCR Threshold Cycle (Ct) Value, one or more other elbow points, or both the Ct Value and the other one or more elbow points, in a curve that depicts the progress of a PCR process that the samples is subject to, say using a Monotonicity Test, or another method, as known in the art. The Ct Value, one or more of the elbow points, or a value derived therefrom, may thus serve as the rank for the sample.

In the third example, the curve is calculated for the sample, by the rank calculator 120, based on the fluorescence values measured during the PCR Reaction that the sample is subject to, and the respective time of measurement or cycle number of each one of the measured values, as described in further detail hereinbelow.

The apparatus 1000 further includes a pair finder 130, in communication with the rank calculator 120.

The pair finder 130 finds among the samples, at least one pair of samples.

Each one of the pairs found by the sample finder 130 includes samples classified into different ones of the classes, and none of the samples (if any) having a calculated rank in between the ranks calculated for the two samples of the found pair are classified into one of the classes.

That is to say that each of the found pairs defines a gap among the ranks calculated for the samples—i.e. a region of uncertainty as to the borderline between classes in terms of rank values, and thus a gap in a classification model evolving based on the results obtained for the samples, through the steps of the method.

The apparatus 1000 further includes a least close pair identifier 140, in communication with the pair finder 130.

The least close pair identifier 140 identifies a pair that includes two samples that are least close to each other in their calculated ranks among the found pairs, thus identifying the widest gap in the evolving model, as described in further detail hereinbelow.

Optionally, the apparatus 1000 further includes a classification obtainer (not shown) in communication with the least close pair identifier 140.

The classification obtainer obtains data on classification of a sample of a calculated rank closest to an average of the ranks calculated for the samples in the identified pair, as described in further detail hereinbelow.

Optionally, the data on the classification of the sample of the calculated rank closest to the average of the ranks calculated for the samples of the identified pair is obtained from a user of apparatus 1000—say from a user who is a PCR Expert, an HPLC Expert, etc., as described in further detail hereinbelow.

Optionally, the data on the classification of the sample of the rank closest to the average is obtained by retrieving the data from a database.

In one example, the database is shared and updated by medical teams in a geographical area in which an Ebola outbreak erupts. In the example, the database is updated with data on classification of a sample whenever a person from whom the sample originates is diagnosed with Ebola or is rather clinically found to be clearly free of Ebola (say in a clinical examination).

That is to say that in the example, the data on the result of the sample that originates from the person is received by the data receiver 110 when the person neither shows any symptom nor is clinically found to be clearly free of Ebola. Only later on, is the data on the classification of the person's sample—say as positive, as negative, or as ambiguous—present in the database, and can thus be retrieved from the database by the classification obtainer.

Optionally, the classification obtainer obtains the data on the classification of the sample of the rank closest to the average calculated for the samples in the identified pair according to heuristics. The heuristics may be predefined, say by a programmer, administrator, or user of apparatus 1000.

Thus, based on the heuristics, the classification obtainer may classify the sample of the rank closest to the average into one of the classes, as described in further detail hereinbelow.

The gap defined by the identified pair is thus divided into two smaller gaps.

Following that obtaining of the data on the classification of the sample of the rank closest to the calculated average, all the samples for which data is received by the data receiver 110 are subjected again to the ranking by the rank calculator 120, finding by the pair finder 130, identifying by the least close pair identifier 140, and possibly, also the obtaining by the classification obtainer.

That is to say that optionally, following that obtaining, the sequence of the steps of ranking, finding, identifying, and possibly, obtaining too, may be iterated over until there is no sample with a calculated rank in between a last identified pair of samples that are least close among pairs found by the pair finder 130, as described in further detail hereinbelow.

The apparatus 1000 may further include an instruction generator 150, in communication with the least close pair identifier 140.

Optionally, when none of the samples for which the data is received by the data receiver 110 have a calculated rank in between the ranks calculated for the identified pair, the instruction generator 150 generates instructions for mixing between one or more pairs of samples qualitatively identical to the identified pair. Using the mixing, there is yielded a respective new sample per each pair of samples thus mixed.

The samples qualitatively identical to the identified pair are samples each of which originates with one of the samples in the identified pair—i.e. a sample divided or subdivided from one of the samples of the identified pair.

A sample qualitatively identical to one of the identified pair's samples may thus be, for example, a sample divided from the identified pair's sample, a sample divided from a sample divided from the identified pair's sample, a sample divided from the later sample, etc., as described in further detail hereinbelow.

Thus, with the instruction generator 150, upon automatically identifying a gap in the evolving classification model by identifying that pair that consists of samples that are least close to each other in their calculated ranks among the found pairs, the apparatus 150 generates instructions for mixing at least one pair of samples qualitatively identical to the identified pair.

The mixing is believed to yield a respective new sample that is likely to be calculated a rank in between the ranks of the two samples of the identified pair, as described in further detail hereinbelow. The gap is thus likely to be narrowed by the new sample.

Optionally, the generated instructions are for preparing a series of new samples, by mixing at least two pairs of samples qualitatively identical to the identified pair, each pair of samples being mixed with each other in a different ratio. The ratios may be defined in advance, say by a programmer, user or operator of apparatus 1000, as described in further detail hereinbelow.

Optionally, after the mixing, the new samples created by the mixing are subject the chemical process, and data on a result obtained for each respective one of the samples using the chemical reaction, is sent to the data receiver 110.

Optionally, the data receiver 110 receives the data on the results obtained for the new samples, and the ranking of the samples, finding of the pairs, identifying of the pair of least close samples among found, and possibly, the obtaining of the data on the classification or the generation of instructions, are performed again, as described in further detail hereinbelow.

Thus, with the present invention, a machine (say a pipetting robot or another laboratory robot) may be instructed to mix samples in a way which iteratively narrows down gaps in the evolving classification model, as described in further detail hereinbelow.

The narrower are the gaps, the more accurate the classification model becomes and the more likely the classification model is to comply with standards defined by the FDA or by one of the other governmental and intergovernmental agencies, as described in further detail hereinbelow.

Optionally, the instruction generator 150 conditions the generation of the instructions for mixing at least one pair of samples identical to the identified pair to yield a respective new sample according to a predefined criterion (say a threshold such as minimal resolution predefined by a programmer, administrator, or operator of apparatus 1000).

In a first example, the criterion is a minimal resolution that is predefined for the chemical process, say by a user of apparatus 1000.

In the first example, the user defines a maximal allowed difference between ranks calculated for samples that undergo a PCR process.

Accordingly, in the first example, when the data received by the data receiver 110 is on results of a PCR process, that user-defined maximal allowed difference is applied on the ranks calculated for the samples of the identified pair, thus serving as the predefined minimal resolution and criterion of the first example.

Per that conditioning by the instruction generator 150, in the example, the instructions are generated only if the difference between the ranks calculated for the samples of the identified pair is higher than the user-defined maximal allowed difference, as predefined for samples that undergo a PCR process.

In a second example, the criterion (say the minimal resolution) is predefined for a machine to be used for the mixing of the samples, say to a specific robot in use for mixing the samples.

In the second example, a user or administrator of apparatus 1000 defines a maximal allowed difference between the calculated ranks of the samples of the identified pair, for the robot that is to be controlled using the instructions.

In the second example, the instruction generator 150 generates the instructions for the machine (say robot), for which machine the minimal resolution is defined, only if the difference between the ranks calculated for the samples of the identified pair is higher than the user-defined maximal allowed difference. The user-defined maximal allowed difference thus serves as the predefined minimal resolution and criterion of the second example.

Optionally, the apparatus 1000 further includes a reaction apparatus in which the results for the samples for which data is received by the data receiver 110 are obtained using the chemical reaction, as described in further detail, for example using FIG. 3, hereinbelow.

Figure 2:
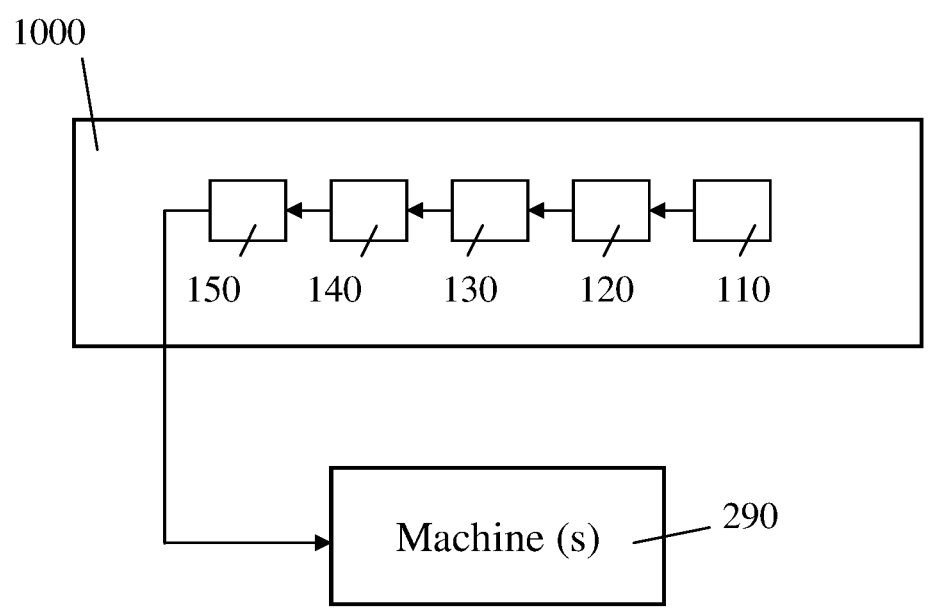
FIG. 2 is a block diagram schematically illustrating a second exemplary apparatus for controlling the mixing of a plurality of samples subject to a chemical process, according to an exemplary embodiment of the present invention.

Reference is now made to FIG. 2, which is a block diagram schematically illustrating a second exemplary apparatus for controlling the mixing of a plurality of samples subject to a chemical process, according to an exemplary embodiment of the present invention.

A second exemplary apparatus for controlling the mixing of a plurality of samples subject to a chemical process may be implemented using electric circuits, computer software, computer hardware, one or more machines (say robots), etc., as described in further detail hereinbelow.

The second apparatus includes Apparatus 1000, as described in further detail hereinabove.

As a part of the second apparatus, apparatus 1000 may be implemented on a computer (say computer chip, or an industrial controller) in communication with one or more machines 290—say one or more robots in use in a laboratory.

Thus, in one example, the apparatus 1000 is implemented on a computer chip that is a part of a computerized controller (such as a computerized controller used in a chemical laboratory)—say a controller which controls one or more robots 290 that are used for mixing samples in a laboratory.

The apparatus 1000 may thus include at least one computer processor.

The apparatus 1000 further includes the one or more additional parts described in further detail hereinabove, such as the parts denoted 110-150 and the classification obtainer, as described in further detail hereinabove.

The second apparatus further includes one or more machines 290 controlled by apparatus 1000 using the instructions generated by the instruction generator 150, as described in further detail hereinabove.

Optionally, the one or more machines 290 include one of more robots.

For example, the machines 290 may include liquid handling robots or similar machines—say robots that dispense selected quantities of samples to a common container, mix and stir the content of the container, etc.

With the second apparatus, when none of the samples for which the data is received by the data receiver 110 have a calculated rank in between the ranks calculated for the identified pair, the instruction generator 150 generates instructions for mixing between one or more pairs of samples qualitatively identical to the identified pair, as described in further detail hereinabove.

The instructions generated by the instruction generator 150 are used to control the machine (say robot 290), say using one or more electric circuits, as known in the art of industrial controlling, so as to control a mixing of the samples qualitatively identical to the identified pair by the robot 290.

The samples qualitatively identical to the identified pair are samples each of which originates with one of the samples in the identified pair—i.e. a sample divided or subdivided from one of the samples of the identified pair.

A sample qualitatively identical to one of the identified pair's samples may thus be, for example, a sample divided from the identified pair's sample, a sample divided from a sample divided from the identified pair's sample, a sample divided from the later sample, etc., as described in further detail hereinabove.

Thus, upon automatically identifying a gap in the evolving model by identifying that pair of samples that are least close to each other in their calculated ranks among the found pairs, the apparatus 1000 control the machine 290, for mixing at least one pair of samples qualitatively identical to the identified pair.

The mixing is believed to yield a respective new sample that is likely to be calculated a rank in between the ranks of the two samples of the identified pair. The gap is thus likely to be narrowed by the new sample, as described in further detail hereinabove.

Optionally, based on the generated instructions, the machine (say robot) 290 mixes at least two pairs of samples qualitatively identical to the identified pair, each pair of samples being mixed with each other in a different ratio.

The ratios may be defined in advance, say by a programmer, user or operator of apparatus 1000, as described in further detail hereinbelow.

Thus, with the present invention, one or machines (say a laboratory robot) 290 may be instructed to mix samples in a way which iteratively narrows down gaps in the evolving classification model, as described in further detail hereinabove.

Optionally, the instruction generator 150 conditions the generation of the instructions for mixing the samples identical to the identified pair, upon a predefined criterion (say the minimal resolution), as described in further detail hereinabove.

Figure 3:
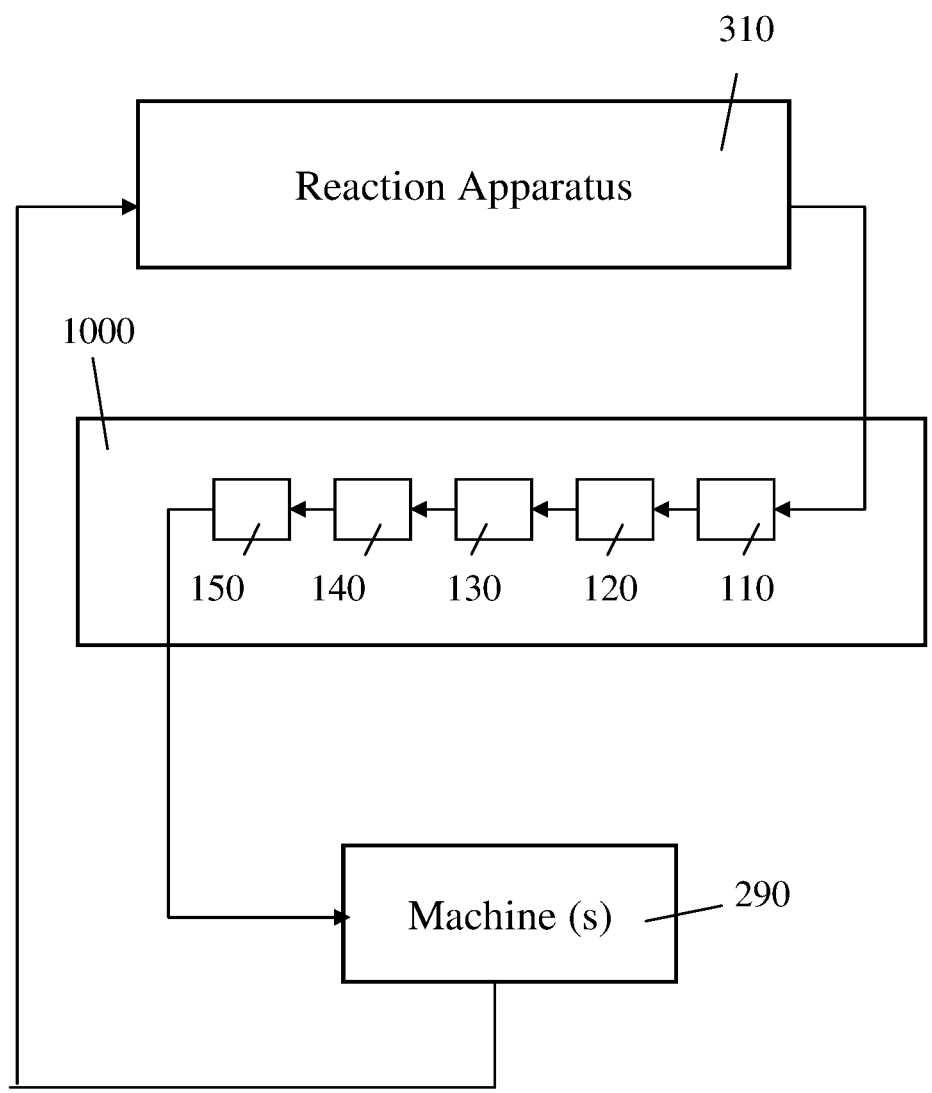
FIG. 3 is a block diagram schematically illustrating a third exemplary apparatus for controlling the mixing of a plurality of samples subject to a chemical process, according to an exemplary embodiment of the present invention.

Reference is now made to FIG. 3, which is a block diagram schematically illustrating a third exemplary apparatus for controlling the mixing of a plurality of samples subject to a chemical process, according to an exemplary embodiment of the present invention.

A third exemplary apparatus for controlling the mixing of a plurality of samples subject to a chemical process may be implemented using electric circuits, computer software, computer hardware, one or more machines (say robots), a chemical apparatus, etc., as described in further detail hereinbelow.

The third apparatus includes apparatus 1000, as wall as one or more machines (say robots) 290 that are controlled for mixing samples, using the instructions generated by the instructor generator 150, as described in further detail hereinabove.

The third apparatus further includes a reaction apparatus 310.

Optionally, the reaction apparatus 310 includes a reaction chamber in which each of the samples for which the data is later received by the data receiver 110, is subject to a chemical process such as PCR or HPLC, as described in further detail hereinabove.

Optionally, the reaction apparatus 310 further includes one or more sensors that measure values of a physical property such an intensity of fluorescence or another quality during or after the chemical process that the sample is subject to, as described in further detail hereinabove.

In a first example, the reaction apparatus 310 is a PCR (Polymerase Chain Reaction) machine (also known as a PCR Cycler) or another instrument used for running a PCR Reaction, as known in the art.

In the first example, the chemical process is thus a PCR process, and the sensors are photometric sensors installed in proximity of the reaction chamber. The photometric sensors measure intensity of light emitted from the reaction chamber, as the PCR process progresses. The photometric sensors may measure the emission of light (i.e. fluorescence values) from the reaction chamber using standard fluorescence methods, as known in the art.

In the example, the reaction apparatus 310 further includes a cycle counter that is connected to the sensors.

The cycle counter instructs the sensors to take measurement of the fluorescence intensity, say once in an interval of time. Optionally, the interval of time and hence the length of each cycle, is predefined by a user, as known in the art.

In the example, the reaction apparatus 310 further includes an Analog-to-Digital (A2D) converter that is connected to the sensors. The Analog-to-Digital (A2D) converter converts the measured fluorescence intensity values into a digital format.

In the example, the reaction apparatus 310 further includes a data accumulator in communication with the A2D converter.

The data accumulator receives the measured values from the A2D converter and stores the measured values. The data accumulator may include, but is not limited to a CD-ROM, a Flash Memory, a RAM (Random Access Memory), etc., as known in the art.

The reaction apparatus 310 further includes a communications module—say a one which includes a communications card that is connected to the data accumulator, and a processor which implements a GUI (Graphical User Interface) on a screen (say a small LCD screen, as known in the art) that is in communication with the processor.

In the example, using the GUI, an operator of the reaction apparatus 310 instructs the communications card to communicate the data accumulated by the data accumulator (i.e. the data on the result of the chemical process that the specific sample is subject to) to the data receiver 110.

Using data received by the data receiver 110 on the result obtained that way for each respective one of two or more samples subject to the PCR process, the instruction generator 150 generates the instructions for the mixing by the machines (say the robot).

Optionally, the instruction generator 150 further forwards the generated instructions to the machines (say robots) 290 used for mixing the samples qualitatively identical to the samples identified by the least close pair identifier 140, as described in further detail hereinabove.

Optionally, the new sample created by the mixing of the samples qualitatively identical to the samples identified by the least close pair identifier 140, is then forwarded to the reaction apparatus 310.

In one example, the sample is forwarded to the reaction apparatus 310 by a robot that is instructed by the instruction generator 150 to take the new sample and pour the new sample into a reaction chamber of the reaction apparatus 310.

In the example, after the new sample is poured into the reaction chamber, the instruction generator 150 further controls the reaction apparatus 310, so as to initiate a PCR process that the new sample is thus subject to.

Further in the example, when the chemical process appears to end, the instruction generator 150 further communicates with the communications module of the reaction apparatus 310, for receiving data on a result of the chemical process.

Consequently, the data on the result (say the fluorescence values accumulated during the PCR process and a respective time of measurement of each of the values) obtained for the new sample, is received by the data receiver 110.

The data received for the new sample thus adds to the data received earlier on results obtained for samples subjected earlier to the chemical process.

Then, both the data received on the result of the new assay and the data previously received on the other samples, are subject to a ranking, finding of pairs, identifying of a pair of least close samples, and possibly, a mixing of samples qualitatively identical to the identified pair, or an obtaining of classification data.

The secondary apparatus may thus implement the steps of an exemplary method as described in further detail and illustrated using FIG. 4 hereinbelow.

Figure 4:
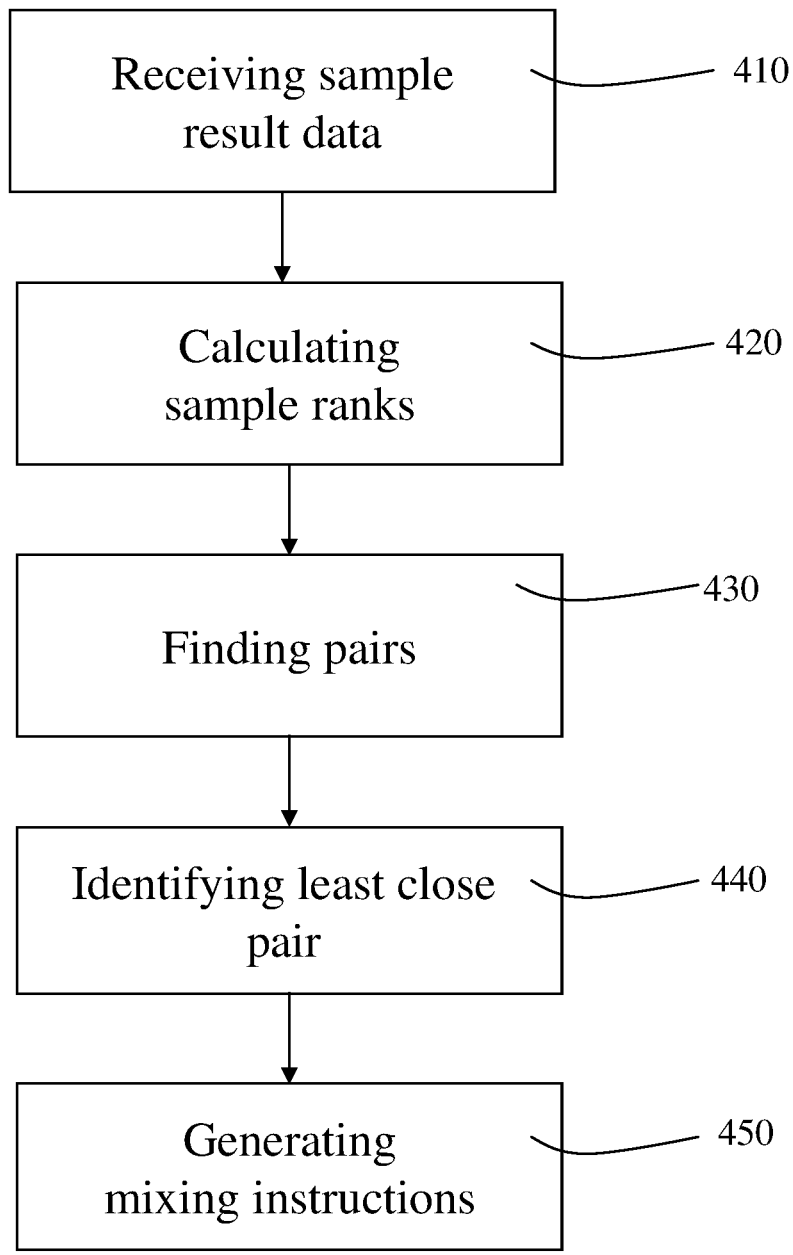
FIG. 4 is a flowchart schematically illustrating an exemplary method for controlling the mixing of a plurality of samples subject to a chemical process, according to an exemplary embodiment of the present invention.

Reference is now made to FIG. 4, which is a flowchart schematically illustrating an exemplary method for controlling the mixing of a plurality of samples subject to a chemical process, according to an exemplary embodiment of the present invention.

An exemplary method for controlling the mixing of a plurality of samples subject to a chemical process may be implemented using electric circuits, computer instructions, etc.

The method may be implemented for example, on a remote server computer, or on a computer chip connected to a machine, installed on the machine, or in remote communication with the machine, etc., as described in further detail hereinabove.

The machine may be for example, a laboratory device such as a robot used to mix samples in a laboratory, a chemical reaction apparatus, etc., as described in further detail hereinabove.

For example, the method may be implemented on a computerized controller in communication with a machine (say a robot), with a reaction apparatus (say a PCR Cycler or an HPLC Instrument), or with both the machine and the reaction apparatus, as described in further detail hereinabove.

In the exemplary method, there is received 410 respective data on a result obtained for each one of two or more samples. For example, the data may be received 410 by the data receiver 110 of apparatus 1000, as described in further detail hereinabove.

The result may be obtained, for example, using a chemical process—say a PCR (Polymerase Chain Reaction) Process or a HPLC (High Performance Liquid Chromatography) process, as described in further detail hereinabove.

Thus, in a first example, the data received 410 on the result includes physical parameter values such as fluorescence intensity values measured over a reaction chamber of a reaction apparatus (say a PCR Cycler) in which the sample is subject to a PCR process, during the PCR process, as described in further detail hereinabove.

In the first example, there is further received 410 a respective time of measurement of each respective one of the fluorescence intensity values, or a temperature measured in the chamber in which the PCR process takes place when each respective one of the fluorescence intensity values is measured.

In a second example, the chemical process is a HPLC (High Performance Liquid Chromatography) process. In the second example, a chemical process apparatus in use is a HPLC instrument which includes a sampler, a pump, an analytical column, one or more detectors, and a microprocessor. The detectors may include, but are not limited to a UV-Vis Absorbance Detector, a Chromatography Detector, etc., as known in the art.

The sampler brings the sample into a mobile phase stream which carries the sample into the analytical column, and the pump delivers the desired flow and composition of the mobile phase through the analytical column.

In the example, each detector generates a signal proportional to the amount of a specific component or a specific component type present in the sample when the sample emerges from the analytical column, as known in the art.

Further in the example, the signals generated by the detectors are processed by the HPLC instrument's microprocessor, to yield the data on the result for the sample, hence providing for quantitative analysis of the sample.

For example, the HPLC instrument's microprocessor may encode the result in the yielded data as a set of numerical values that indicate the presence and amount of each one of the specific components or component types present in the sample when the sample emerges from the analytical column.

Then, the data on the result for the sample is communicated from the HPLC Instrument (say over a Local Area Network or a Wide Area network) and is received 410 say by the data receiver 110 of apparatus 1000, as described in further detail hereinabove.

Further in the exemplary method, for each one of at least two of the samples, there is further received 410 respective data on classification of the sample into one of at least two classes (say as Negative or rather as Positive) beforehand (i.e. before the data on the results is received 410), as described in further detail hereinbelow.

Thus, in a first example, a few of the samples are classified according to clinical symptoms. In the example, for each one of the few classified sample, there is received 410 data on classification of the sample as positive or negative, based on clinical symptoms expressed by a specific person from whom the sample is obtained.

In a second example, the few samples are rather classified by an expert through manual examination of the result obtained for each respective one of the few samples.

For example, a PCR Expert may classify each respective one of the few samples based on a curve that depicts the course of a PCR Reaction that the sample is subject to, say as fluorescence values per time of the reaction, so as to obtain the result for the sample, as known in the art.

Similarly, a HPLC Expert may classify each respective one of the few samples based on a result obtained for the sample using a HPLC process carried out using an HPLC Instrument, as described in further detail hereinabove.

Optionally, one of the classes is simply a class of samples found to be non-classifiable into any one of the remaining classes, which class may also be referred to as a class of Ambiguous Samples.

Thus, in a first example, the class of Ambiguous Samples includes samples obtained from persons who appear sick but have clinical symptoms characteristic of several different diseases, and therefore cannot be categorically classified as Positive or Negative with respect to a specific disease based on their clinical symptoms alone.

In a second example, the class of Ambiguous Samples includes samples that a PCR or a HPLC Expert hired to classify some of the samples beforehand, tries to classify but finds to be confusing (say due to contradictory findings in the results, as known in the art) and thus ambiguous.

The remaining samples are samples that are not classified yet (i.e. samples that are not even found to be unclassifiable), say because the remaining samples belong to people who do not express clinical symptoms yet, or because the number of samples is too high for a PCR or HPLC Export to classify in time.

Indeed, during an outbreak of a new life threatening disease, many hundreds or even thousands of samples may need to be taken from people who live in a wide geographical area over which the disease appears to spread rapidly.

During such a outbreak, the hundreds or thousands of samples may need to be used to develop a classification mode quickly, while most of the people from whom the samples are taken do not express any clinical symptom typical of the disease yet and Experts available on site do not have enough time to classify more than a few dozens of the samples using the results.

In one example, the exemplary method further includes a step in which the data received 410 on the result is used to represent each sample as a point in a mathematical embedded space, say by the rank calculator 120. Consequently, each point in the embedded space is a parameterized representation of the result obtained for a specific one of the samples using the chemical reaction.

In a second example, the received 410 data already includes the position of a point representative of the result obtained for the respective sample in a mathematical embedded space, and is thus a parameterized representation of the sample subject to the chemical reaction used to obtain the result for that sample.

Optionally, the exemplary method further includes a step in which the embedded space is subject to a process of dimensionality reduction, say using diffusion mapping, as known in the art.

In the exemplary method, for each one of the samples, there is calculated 420 a respective rank based at least on the result obtained for the sample using the chemical process, according to a predefined formula, rule, parameter, etc., say by the rank calculator 120 of apparatus 1000, as described in further detail hereinabove.

For example, the method may include as step of identifying in the received 410 data on the results, a most significant parameter or a combination of two or more most significant parameters, and a calculation 420 of the rank based on the identified most significant parameter or combination of most significant parameters.

The most significant parameter may be, a dimension of the embedded space, along which dimension the points' positions have a maximal variance, a parameter usually relied on for classifying samples using the chemical reaction used to obtain the results—say a PCR Ct (Threshold Cycle), etc., as known in the art.

In one example, the most significant parameter is identified during the dimensionality reduction of the embedded space.

For example, in some dimensionality reduction techniques, the most significant parameter may be a most significant dimension arrived at during the dimensionality reduction, say a Fiedler Vector. The Fiedler Vector is an eigenvector associated with algebraic connectivity and is thus an indicator which may show which points are likely to belong to a same class, as known in the art of Algebraic Connectivity.

In a second example, only for some of the samples, is there received 420 data on classification into one of two or more classes, as described in further detail hereinabove. In the example, a Support Vector Machine (SVM) or another affinity measuring algorithm (such as the Logistics Classifier) may be used to find the most significant parameter that may be, for example, the discriminating function calculated during SVM, as known in the art.

Then, there is found 430 among the samples, one or more pairs of samples, say by the pair finder 130 of apparatus 1000, as described in further detail hereinabove.

Each one of the found 430 pairs includes samples classified into different ones of the classes. However if there are, among the remaining samples, any samples that have a calculated 420 rank in between the ranks calculated 420 for the samples included in the found 420 pair, none of those samples are classified into any one of the classes (i.e. not even to a class of Ambiguous Samples).

Thus, each one of the found 430 pairs defines an uncertainty region of samples—i.e. a series of samples that may include only unclassified samples with calculated 420 ranks that are in between the ranks calculated 420 for the two samples of the found 430 pair. The two samples of the found 430 pair thus define that uncertainty region, as illustrated using FIG. 5A-5E hereinbelow.

That is to say that each of the found 430 pairs defines a gap among the ranks calculated 420 for the samples—i.e. a region of uncertainty as to the borderline between classes in terms of rank values, and thus a gap in a classification model evolving based on the results obtained for the samples, through the steps of the method.

Reference is thus diverted to FIG. 5A-5E, which are simplified diagrams each of which schematically illustrates exemplary uncertainty regions, according to an exemplary embodiment of the present invention.

In FIG. 5A-5E, for the purpose of schematic illustration, the samples are represented by a plurality of dots arranged along a line which represents a range of rank values. Each point is positioned on the line, in a position which reflects the rank calculated 420 for the sample represented by the point, and thus, the closer the point is to the right end of the line, the higher is the rank calculated 420 for the sample represented by the point.

Figure 5A:
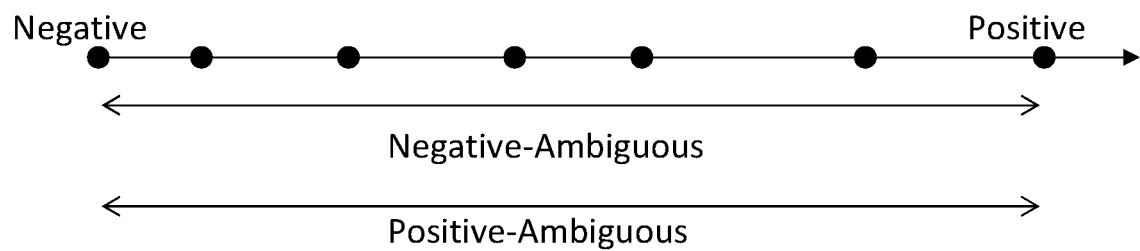
FIG. 5A is a simplified diagram schematically illustrating a first example of uncertainty regions, according to an exemplary embodiment of the present invention.

In a first example, as illustrated in FIG. 5A, only two of the samples are classified.

More specifically, the rightmost point represents a sample classified as Positive, whereas the leftmost point represents a sample classified as Negative, and none of the remaining samples are classified yet.

In the first example, the pair of classified points defines an uncertainty region of samples. The defined uncertainty region spans all samples with ranks that are in between the ranks calculated 420 for the only sample classified as Positive and the only sample classified as Negative. The uncertainty region may also be referred to as a Positive-Ambiguous Uncertainty Region or as a Negative-Ambiguous Uncertainty Region.

Figure 5B:
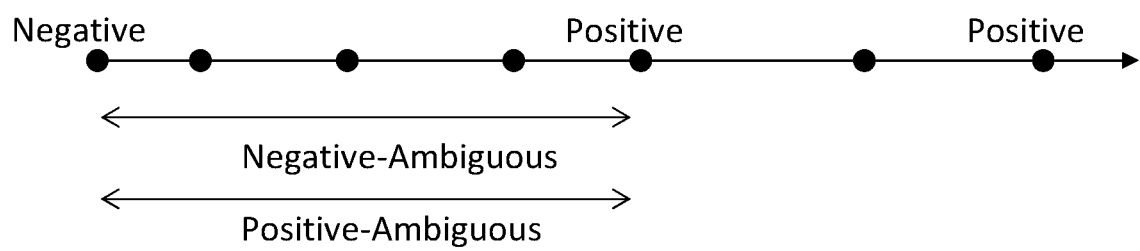
FIG. 5B is a simplified diagram schematically illustrating a second example of uncertainty regions, according to an exemplary embodiment of the present invention.

In a second example, as illustrated in FIG. 5B, three of the samples are classified. More specifically, two of the points represent samples classified as Positive, only one of the points represents a sample classified as Negative, and none of the remaining samples are classified yet.

In the example, the leftmost point representing a sample classified as Positive and the only point representing a sample classified as Negative define an uncertainty region of samples. The uncertainty region defined by those two points spans all samples with ranks in between the ranks calculated 420 for those two points. In this example too, the uncertainty region may also be referred to as a Positive-Ambiguous Uncertainty Region or as a Negative-Ambiguous Uncertainty Region.

Figure 5C:
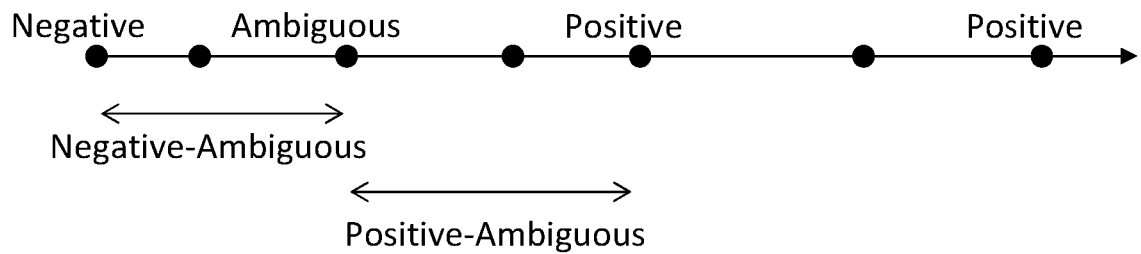
FIG. 5C is a simplified diagram schematically illustrating a third example of uncertainty regions, according to an exemplary embodiment of the present invention.

In a third example, as illustrated in FIG. 5C, four of the samples are classified. More specifically, two of the points represent samples classified as Positive, and one of the points represents a sample classified as Negative. Further in the example, one of the points represents a sample classified as Ambiguous (say due to confusing clinical symptoms or results, as described in further detail hereinabove), and none of the remaining samples are classified yet.

In the example, the leftmost point representing a sample classified as Positive and the only point that represents a sample classified as Ambiguous define a first uncertainty region of samples. The first uncertainty region spans all samples with calculated 420 ranks in between the ranks calculated 420 for those two points. Further, the only point that represents a sample classified as Ambiguous and the only point that represents a sample classified as Negative define a second uncertainty region of samples. The second uncertainty region spans all samples with ranks in between the ranks calculated 420 for those two points. The two regions may also be referred to as a Positive-Ambiguous Uncertainty Region and a Negative-Ambiguous Uncertainty Region, respectively.

Figure 5D:
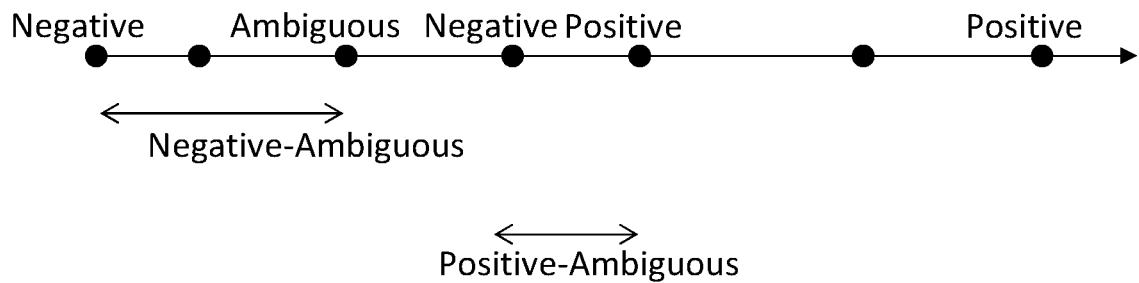
FIG. 5D is a simplified diagram schematically illustrating a fourth example of uncertainty regions, according to an exemplary embodiment of the present invention.

In a fourth example, as illustrated in FIG. 5D, five of the samples are classified. More specifically, two of the points represent samples classified as Positive and two of the points represent samples classified as Negative. Further in the example, one point positioned between the two points that represent Negative samples, represents a sample classified as Ambiguous (say due to confusing clinical symptoms or results), and none of the remaining samples are classified yet.

In the example, the leftmost point representing a sample classified as Positive and the rightmost point that represents a sample classified as Negative define a first uncertainty region of samples. Further, the only point that represents a sample classified as Ambiguous and the remaining point that represents a sample classified as Negative (i.e. the leftmost point) define a second uncertainty region. The regions may also be referred to as a Positive-Ambiguous Uncertainty Region and a Negative-Ambiguous Uncertainty Region, respectively.

Figure 5E:
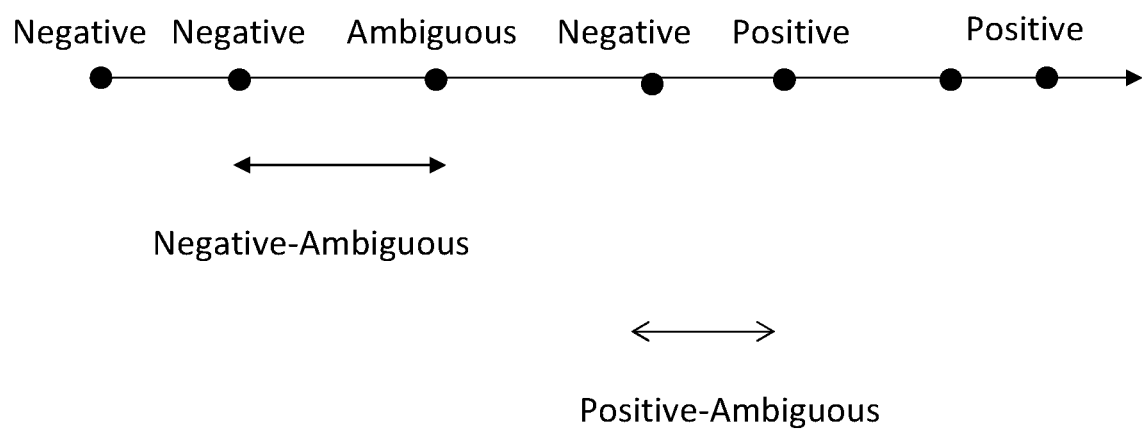
FIG. 5E is a simplified diagram schematically illustrating a fifth example of uncertainty regions, according to an exemplary embodiment of the present invention.

In a fifth example, as illustrated in FIG. 5E, six of the samples are classified. More specifically, two of the points represent samples classified as Positive and three of the points represent samples classified as Negative. Further in the example, one point positioned between two points that represent Negative samples, represents a sample classified as Ambiguous (say due to confusing clinical symptoms or results), and none of the remaining samples are classified yet.

In the example, the leftmost point representing a sample classified as Positive and the rightmost point that represents a sample classified as Negative define a first uncertainty region of samples. Further, the only point that represents a sample classified as Ambiguous and the second point from the left—a point that represents a sample classified as Negative—define a second uncertainty region. The regions may also be referred to as a Positive-Ambiguous Uncertainty Region and a Negative-Ambiguous Uncertainty Region, respectively.

Reference is now returned to FIG. 4.

Next, in the exemplary method, there is identified 440 a pair which includes two samples that are least close to each other in their calculated 420 ranks among the found 430 pairs, say using the least close pair identifier 140 of apparatus 1000, as described in further detail hereinabove.

The identified pair of samples defines the widest gap in the evolving classification model, as described in further detail hereinabove.

Optionally, the exemplary method further comprises an additional step in which there is obtained data on classification of a sample of a calculated 420 rank closest to an average of the ranks calculated 420 for the samples in the identified 440 pair.

In one example, the data on the classification of the sample of the calculated 420 rank closest to the average of the ranks calculated 420 for the samples in the identified 440 pair is obtained from a user of apparatus 1000—say a user who is a PCR Expert, a HPLC Expert, etc. For example, the PCR Expert may calculate or be presented a reaction curve calculated from the data received 410 on the sample's result (say by the rank calculator 140), and asked to classify the sample as Positive, Negative, or Ambiguous, based on the presented curve.

In a second example, the data on the classification of the sample of the rank closest to the average is obtained by retrieving the data from a database.

In the second example, the database may be a database shared and updated by medical teams in a geographical area in which an Ebola outbreak erupts. The database is updated whenever a person from whom one of the received 410 samples originates, is diagnosed with Ebola or is rather clinically found to be clearly free of Ebola (say in a clinical examination).

That is to say that in the example, the data on the result obtained for the sample that originates from the person is received 410 by apparatus 1000 before the person shows any symptom or is clinically found to be clearly free of Ebola. Only later on, when the additional step is carried out, is the data on the classification of that sample—say as positive, negative, or ambiguous—present in the database.

In a third example, the data on the classification of the sample having the calculated 420 rank closest to the average calculated for the samples in the identified 440 pair is obtained according to predefined heuristics. In the example, the heuristics is defined in advance of the receipt 410 of the data, say by a programmer, administrator, or user of apparatus 1000. Based on the predefined heuristics, the sample of the calculated 420 rank closest to the average is classified into one of the classes.

In one example, the heuristics is based on Signal-to-Noise Ratio (SNR). In the example, there is calculated an SNR value per each sample for which the data is received 410.

In the example, there is subtracted a baseline calculated for a curve that depicts the progress of the PCR process that involves the sample from the maximal fluorescence intensity value measured during that PCR process.

The baseline may be calculated, for example, by applying a monotonicity test on the curve, to find an early part of curve which precedes the point in which the chemical process begins, and applying linear regression on that early part of the curve, as known in the art.

Then, the result of the subtraction is divided by a standard deviation of the fluorescence intensity values measured during that PCR process, to yield the SNR value. When the SNR value is higher than a predefined range of values, the sample is classified as positive, and when the SNR value is lower than a predefined range of values, the sample is classified as positive. Otherwise (i.e. when the SNR value is within the predefined range), the sample is classified as Ambiguous.

In a second example, the result of the subtraction of baseline from the maximal fluorescence intensity value itself is compared to a predefined RFU (Relative Fluorescence Unit) threshold. When the result of the subtraction is higher than the RFU threshold, the sample is classified as Positive, whereas when the result of the subtraction is lower than the RFU threshold, the sample is classified as negative.

In a third example, the heuristics is based on a predefined Ct (Threshold Cycle) value range. When the PCR process that involves the sample has a Ct value within that predefined Ct range, the sample is classified as Positive, whereas when the Ct value is not within that predefined Ct range, the sample is classified as Negative.

The gap defined by the identified 440 pair is thus divided into two smaller gaps.

Following the obtaining of the data on the classification of the sample of the calculated 420 rank closest to the calculated average, there are performed again the steps of ranking 420, finding 430, identifying 440, and possibly, the additional step too.

Optionally, following that obtaining, steps 420-440 and possibly, the step of obtaining the classification data, are iterated over time and again, until there is no sample with a calculated 420 rank in between the last identified 440 pair of samples that are least close among found 430 pairs, as described in further detail hereinbelow.

Optionally, when none of the samples for which the data is received 410 have a calculated 420 rank in between the ranks calculated 420 for the identified 440 pair, there are generated 450 instructions for mixing between one or more pairs of samples qualitatively identical to the identified 440 pair, to yield a respective new sample.

Optionally, the instructions are generated 450 by the instruction generator 150 of apparatus 1000, as described in further detail hereinabove.

The samples qualitatively identical to the identified 440 pair are samples each of which is taken from one of the samples in the identified 440 pair—i.e. a sample divided or subdivided from one of the samples of the identified 440 pair.

A sample qualitatively identical to one of the identified 440 pair's samples may be, for example, a sample divided from the identified 440 pair's sample, a sample divided from a sample divided from the identified 440 pair's sample, a sample divided from the later sample and thus subdivided from one of the identified 440 pair's samples, etc.

Thus, upon automatically identifying a gap in the evolving classification model by identifying 440 the pair of samples that are least close to each other in their calculated 420 ranks among the found 430 pairs, there may be generated 450 the instructions for the mixing.

The mixing is believed to yield a respective new sample that is likely to be calculated 420 a rank in between the ranks of the two samples of the identified 440 pair, as described in further detail hereinbelow. The gap is thus likely to be divided into two smaller gaps, thus narrowing down the gaps in the evolving classification model, as described in further detail hereinabove.

Optionally, the generated 450 instructions are for preparing a series of new samples, by mixing at least two pairs of samples qualitatively identical to the identified pair, each pair of samples being mixed with each other in a different ratio. The ratios may be defined in advance, say by a programmer, user or operator of apparatus 1000, as described in further detail hereinbelow.

Thus, with the present invention, one or more machines (say a laboratory robot) may be instructed to mix samples in a way which iteratively narrows down gaps among in the evolving classification model, as described in further detail hereinbelow.

The narrower are the gaps in the evolving classification model, the more accurate the classification model becomes and the more likely the classification model is to comply with standards defined by the FDA or by one of the other governmental and intergovernmental agencies, as described in further detail hereinbelow.

Optionally, the generating 450 of the instructions for mixing at least one pair of samples identical to the identified 440 pair to yield a respective new sample is further conditioned according to a predefined criterion—say a minimal resolution predefined by a programmer, administrator, or operator of apparatus 1000.

In a first example, the criterion (say the minimal resolution) is predefined for the chemical process, say by a user of apparatus 1000.

In the first example, the user defines a criterion—say a maximal allowed difference between ranks calculated 420 for samples that undergo a PCR process.

Accordingly, in the first example, when the received 410 results are of a PCR process, that user-defined maximal allowed difference is applied on the ranks calculated 420 for the samples of the identified 440 pair, thus serving as the predefined minimal resolution and the predefined criterion of the first example.

In the example, the instructions are generated 450 only if the difference between the ranks calculated 420 for the samples of the identified 440 pair is higher than the user-defined maximal allowed difference, as predefined for samples that undergo a PCR process.

In a second example, the criterion is predefined for a machine to be used for the mixing of the samples, say to a specific robot in use for mixing the samples.

In the second example, a user or administrator of apparatus 1000 defines a maximal allowed difference between the calculated 420 ranks of the samples of the identified 440 pair, for the machine (say the robot) that is to be controlled using the generated 450 instructions.

In the second example, the instructions for the machine, for which machine the minimal resolution is defined, are generated 450 only if the difference between the ranks calculated 420 for the samples of the identified 440 pair is higher than that user-defined maximal allowed difference, as predefined for the machine.

Optionally, a part of the mixing or a forwarding of the generated 450 instructions to a machine is carried out by a laboratory technician, a user or operator of apparatus 1000, etc.

Optionally, the exemplary method further includes a preliminary step of running the chemical process on each sample for which the respective data is later received 410, say using a reaction apparatus, as described in further detail hereinabove.

Optionally, the exemplary method further includes a preliminary step of running a PCR process on each sample for which the respective data is later received 410, for obtaining the result (say the fluorescence values and a corresponding time or temperature for each fluorescence value), as described in further detail hereinabove.

Optionally, the exemplary method further includes a step of deriving the results from measurements made during the chemical process—say from the fluorescence values and the corresponding time or temperature for each fluorescence value, as described in further detail hereinabove.

In one example, the chemical process is a PCR process and the exemplary method includes a step of identifying a respective threshold value (Ct) point in each specific one of several curves. Earlier in the step, each one of the curves is generated based on the fluorescence values and corresponding time or temperature and depicts the progress of the PCR Process for a respective one of the samples—i.e. the fluorescence value per time or temperature.

The result may thus be a Ct point identified using any one of the methods known in the art, say using one of the monotonicity methods, as known in the art.

Similarly, in a second example, the result may include two or more elbow points, and the method may include a step in which the elbow points (i.e. the result) are identified in the curves that depict the fluorescence value per time or temperature, using one of the methods known in the art.

Figure 6:
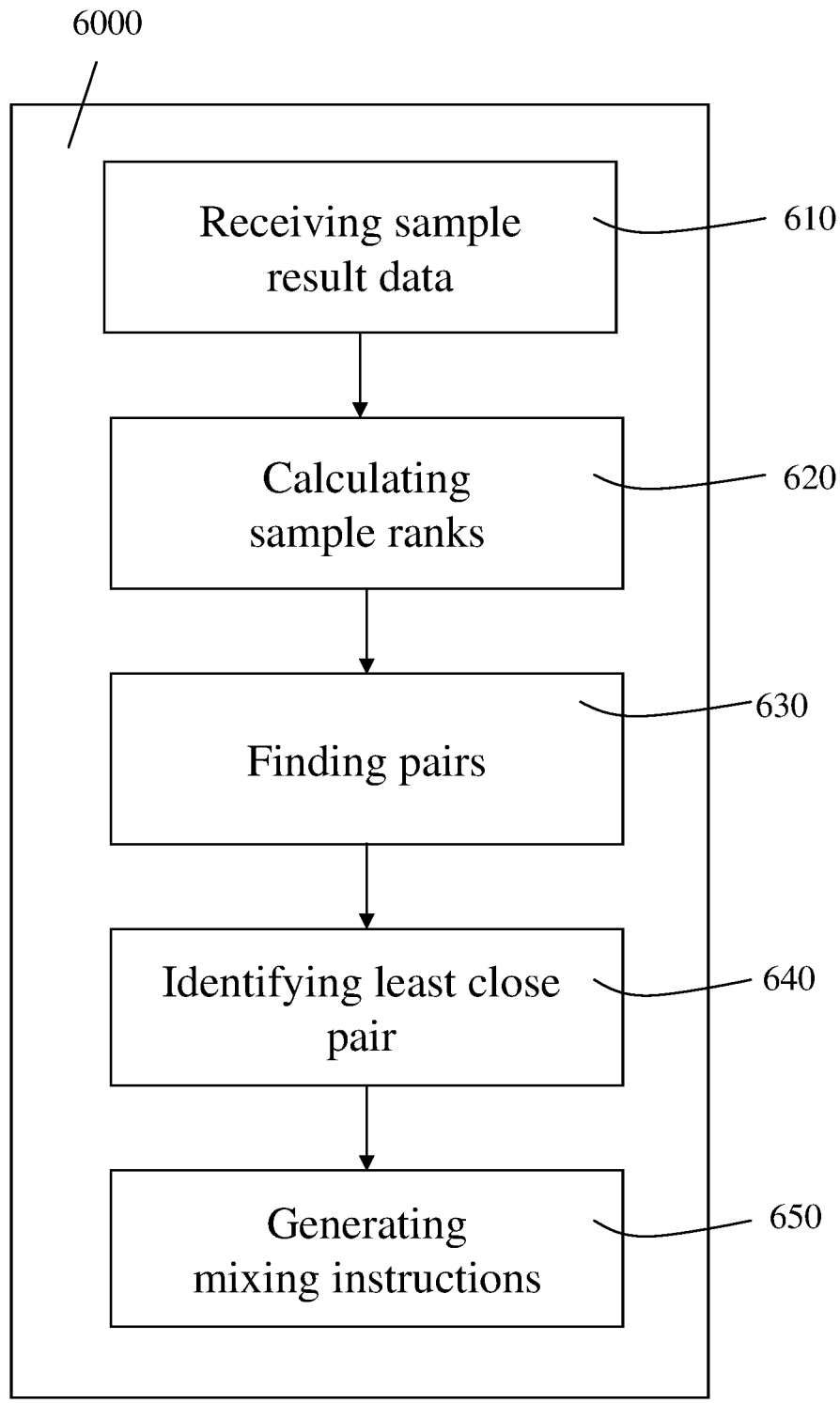
FIG. 6 is a block diagram schematically illustrating a non-transitory computer readable medium storing computer executable instructions for performing steps of controlling the mixing of a plurality of samples subject to a chemical process, according to an exemplary embodiment of the present invention.

Reference is now made to FIG. 6, which is a block diagram schematically illustrating a non-transitory computer readable medium storing computer executable instructions for performing steps of controlling the mixing of a plurality of samples subject to a chemical process, according to an exemplary embodiment of the present invention.

According to an exemplary embodiment of the present invention, there is provided a non-transitory computer readable medium 6000, such as a Micro SD (Secure Digital) Card, a CD-ROM, a USB-Memory, a Hard Disk Drive (HDD), a Solid State Drive (SSD), a computer's ROM chip, etc.

The computer readable medium 6000 stores computer executable instructions, for performing steps of controlling the mixing of a plurality of samples subject to a chemical process, say according to steps of the exemplary method described in further detail hereinabove, and illustrated using FIG. 4.

The instructions may be executed on one or more computer processors.

The instructions may be executed for example, on a remote server computer, on a computer chip connected to a machine—say to a laboratory device such as a robot used to mix samples in a laboratory, to a reaction apparatus, etc. The computer chip may be installed on the machine, be in remote communication therewith, etc., as described in further detail hereinabove.

Thus, in one example, the instructions may be executed on a computerized controller in communication with the machine (say robot), with a reaction apparatus (say a PCR Reaction Chamber or an HPLC Apparatus), or with both the machine and the reaction apparatus, as described in further detail hereinabove.

The computer executable instructions include a step of receiving 610 data on a result obtained for each respective one of two or more samples, as described in further detail hereinabove.

The result may be obtained, for example, using a chemical process—say a PCR (Polymerase Chain Reaction) Process or a HPLC (High Performance Liquid Chromatography) process, as described in further detail hereinabove.

Thus, in a first example, the data received 610 on the result includes physical parameter values such as fluorescence intensity values measured over a chemical apparatus in which the sample is subject to a PCR Process, during the PCR Process.

In the first example, there is further received 610 a time of measurement of each respective one of the fluorescence intensity values, or a temperature measured in a chamber in which the process takes place when each respective one of the fluorescence intensity values is measured over that chamber.

In a second example, the chemical process is a HPLC (High Performance Liquid Chromatography) process. In the second example, a chemical process apparatus in use is a HPLC instrument which includes a sampler, a pump, one or more detectors, and a microprocessor. The detectors may include, but are not limited to a UV-Vis Absorbance Detector, a Chromatography Detector, etc., as known in the art.

The sampler brings the sample into a mobile phase stream which carries the sample into an analytical column, and the pump delivers the desired flow and composition of the mobile phase through the analytical column, as known in the art.

In the example, each detector generates a signal proportional to the amount of a specific component or of a specific component type present in the sample when the sample emerges from the analytical column.

The signals generated by the detectors are processed by the HPLC instrument's microprocessor, to yield the data on the result obtained for the sample, thus allowing for quantitative analysis of the sample. Then, the data on the result obtained for the sample is communicated from the HPLC Instrument (say over a Local Area Network or a Wide Area network—as known in the art), and is received 610, as described in further detail hereinabove.

Using the computer executable instructions, for each one of at least two of the samples, there is further received 610 data on a classification of the respective sample into one of at least two classes (say as Negative or as Positive), as described in further detail hereinabove.

In a first example, a few of the samples for which the data on the results is received 610 are classified according to clinical symptoms. In the example, for each one of the few classified samples, there is received 610 respective data on a classification of the sample as positive or rather as negative. In the example, the classification of the sample is based on clinical symptoms expressed by a person from whom the sample is obtained, as described in further detail hereinabove.

In a second example, for each one of the few classified samples, there is received 610 data on the classification, as determined by an expert through manual examination of the results obtained for each specific one of the few sample beforehand, as described in further detail hereinabove.

For example, a PCR Expert may classify the sample based on a curve that depicts a course of a PCR Reaction that the sample is subject to, as fluorescence values per time of the reaction, as known in the art.

Similarly, a HPLC Expert may classify the sample based on the result obtained for the sample based on a HPLC process carried out using a HPLC Instrument, as described in further detail hereinabove.

Optionally, one of the classes is simply a class of samples found to be non-classifiable into any one of the remaining classes, which class may also be referred to as a class of Ambiguous Samples.

Thus, in one example, a class of Ambiguous Samples includes samples obtained from persons who appear sick but have confusing clinical symptoms, as described in further detail hereinabove.

In the example, the samples in the class of Ambiguous Samples belong to persons that have confusing clinical symptoms (say symptoms that are characteristic of several different diseases), and therefore cannot be used to categorically classify the samples as Positive or Negative with respect to a specific disease.

In a second example, the class of Ambiguous Samples includes samples that a PCR or HPLC Expert hired to classify some of the samples beforehand, tries to classify but finds to be ambiguous, as described in further detail hereinabove.

The remaining samples are not classified yet, say because the remaining samples belong to people who do not express clinical symptoms yet, because the number of samples is too high for a PCR or HPLC Export to classify in time (say during a rapid outbreak of a disease), etc., as described in further detail hereinabove.

The computer executable instructions further include a step in which, for each one of the samples, there is calculated 620 a respective rank based at least on the result obtained for the sample using the chemical process, say using a predefined formula, as described in further detail hereinabove.

For example, the computer executable instructions may further include a step of identifying, in the received results, a most significant parameter or a combination of two or more most significant parameters. Then, the calculation 620 of the ranks may be based on the identified most significant parameter or combination, as described in further detail hereinabove.

In one example, the most significant parameter is a dimension along which the positions of the points as per the data received 610 on the results of the respective samples have a maximal variance.

In another example, the most significant parameter is a parameter usually relied on for classifying samples using the chemical reaction used to obtain the results—say a Ct (Threshold Cycle) for PCR, etc., as known in the art.

In one example, the most significant parameter is identified during the dimensionality reduction of the embedded space. For example, the most significant parameter is a most significant dimension arrived at during the dimensionality reduction, say a Fiedler Vector, as known on the art.

In a second example, only for some of the samples, is there received 610 data on the classification to one of two or more classes, as described in further detail hereinabove. In the example, a Support Vector Machine (SVM) or another affinity measuring algorithm (such as Logistics Classifier) may be used to find the most significant parameter that may be, for example, the discriminating function calculated during SVM, as known in the art.

The computer executable instructions further include a step of finding 630 among the samples at least one pair of samples.

Each one of the found 630 pairs consists of samples classified into different ones of the classes, and none of the samples (if any) having a calculated rank in between the ranks calculated for the samples included in the found 630 pair are classified into one of the classes.

The computer executable instructions further include a step of identifying 640 a pair that consists of samples that are least close to each other in their calculated 620 ranks among the found 630 pairs of closest samples, as described in further detail hereinabove.

Optionally, the computer executable instructions further include an additional step. In the additional step, there is obtained data on classification of a sample of a rank closest to an average of the ranks calculated 620 for the samples in the identified 640 pair.

In one example, the data on the classification of the sample of the rank closest to the average is obtained from a user—say a PCR Expert, a HPLC Expert, etc., as described in further detail hereinabove.

In a second example, the data on the classification of the sample of the calculated 620 rank closest to the average is obtained by retrieving the data on the classification of a sample of a rank closest to the average from a database.

In the second example, the database may be a database shared and updated by medical teams in a geographical area in which an Ebola outbreak erupts. The database is updated whenever a person from whom one of the samples originates, and on whose sample, data on the result is received 410 earlier, is diagnosed with Ebola.

That is to say that in the example, the data on the result obtained for the sample that originates from the person is received 610 before the person shows any symptom typical of Ebola, and only when the additional step is carried out, is the data on the classification of that sample as positive present in the database.

In a third example, the data on the classification of the sample of the calculated 620 rank closest to the average is obtained according to heuristics predefined, say by a programmer, administrator, or user, as described in further detail hereinabove. Thus, based on the heuristics, the sample of the calculated 620 rank closest to the average is classified into one of the classes.

The computer executable instructions include a step in which, following that obtaining of the data on the classification of the sample of the calculated 620 rank closest to the average, there are performed again the steps of ranking 620, finding 630, identifying 640, and optionally, the additional step too.

Optionally, the sequence of steps 620-640 and optionally, the additional step too, is iterated over until there is no sample with a calculated 620 rank in between the last identified 640 pair of samples, as described in further detail hereinabove.

The computer executable instructions may further include a step in which, when none of the samples for which the data is received 610 have a rank in between the ranks calculated 620 for the identified 640 pair, there are generated 650 instructions. The generated 650 instructions are for mixing one or more pairs of samples qualitatively identical to the identified pair, to yield a respective new sample per each pair of samples being mixed with each other, as described in further detail hereinabove.

The samples qualitatively identical to the identified 640 pair are samples each of which is taken from one of the samples in the identified 640 pair—i.e. a sample divided or subdivided from one of the samples of the identified 640 pair.

For example, a sample qualitatively identical to one of the identified 640 pair's samples may be a sample divided from the identified 640 pair's sample, a sample divided from a sample divided from the identified 640 pair's sample, a sample divided from the later sample, and thus subdivided from one of the identified 640 pair's samples, etc.

Thus, upon automatically identifying a gap in the evolving model by identifying 640 the pair of samples that are least close to each other in their calculated 620 ranks among the found 630 pairs, there are generated 650 instructions for mixing at least one pair of samples qualitatively identical to the identified 640 pair.

The mixing is believed to yield a respective new sample that is likely to be calculated 620 a rank in between the ranks of the two samples of the 640 identified pair, as described in further detail hereinabove. The gap is thus likely to be divided into two smaller gaps, by the new sample, as described in further detail hereinabove.

Optionally, the generated 650 instructions are for preparing a series of new samples, by mixing at least two pairs of samples qualitatively identical to the identified pair, each pair of samples being mixed with each other in a different ratio. The ratios may be defined in advance, say by a programmer, user or operator, as described in further detail hereinbelow.

Thus, with the present invention, a machine (say a laboratory robot) may be instructed to mix samples in a way which iteratively narrows down gaps in the evolving classification model, as described in further detail hereinabove.

Optionally, the computer executable instructions further condition the generating 650 of the instructions upon a predefined criterion, as described in further detail hereinabove.

In a first example, the predefined criterion is a minimal resolution predefined for the chemical process say by a user, as described in further detail hereinabove.

In the first example, the user defines a maximal allowed difference between ranks calculated 620 for samples that undergo a PCR process. Accordingly, in the first example, when the received 610 results are of a PCR process, that user-defined maximal allowed difference is applied on the samples of the identified 640 pair, thus serving as the predefined criterion and the predefined minimal resolution.

In that first example, the instructions are generated 650 only if the difference between the ranks calculated 620 for the samples of the identified 640 pair is higher than the user-defined maximal allowed difference, as predefined for samples that undergo a PCR process.

In a second example, the predefined criterion is a minimal resolution predefined for a machine (say robot) to be used for the mixing of the samples, say to a robot in use for mixing the samples.

In the second example, a user or administrator defines a maximal allowed difference between the calculated 620 ranks of the samples of the identified 640 pair, for the machine that is to be controlled using the generated 650 instructions, as described in further detail hereinabove.

In the second example, the instructions for the machine, for which machine the minimal resolution is defined, are generated 650 only if the difference between the ranks calculated 620 for the samples of the identified 640 pair is higher than that user-defined maximal allowed difference, as described in further detail hereinabove.

Optionally, the computer executable instructions further include a preliminary step of running the chemical process on each sample for which the data is later received 610, say by controlling a reaction apparatus, as described in further detail hereinabove.

Optionally, the computer executable instructions further include a preliminary step of running a PCR (Polymerase Chain Reaction) process on each respective sample for which the data is later received 610, and for obtaining the result for the respective sample. The result may include for example, the measured physical parameter values (say fluorescence values) and the corresponding time or temperature for each one of the measured values, as described in further detail hereinabove.

Optionally, the computer executable instructions further include a step of deriving the results from measurements made during the chemical process—say from the fluorescence values and the corresponding time or temperature for each fluorescence value, as described in further detail hereinabove.

In one example, the chemical process is a PCR process and the computer executable instructions include a step in which a respective Threshold Cycle (Ct) point is identified in each one of several curves, and is thus derived from the measurements. Each one of the curves depicts the progress of the PCR Process for a respective one of the samples—i.e. the fluorescence value (or other measured physical parameter value) per time or temperature. The result may thus be a Ct point identified using any one of the methods known in the art, say using one of monotonicity methods, as known in the art.

Similarly, in a second example, the result may include two or more elbow points, and the computer executable instructions may include a step in which the elbow points are identified in the curves that depict the physical parameter value, say fluorescence value, per time or temperature, using one of the methods known in the art.

General Further Discussion

In an exemplary scenario, a new strand of the Zika Virus is identified in Brazil during an outbreak of the disease in a faraway rural community. A new real-time PCR test is developed to identify and classified the new strand of Zika virus.

In the scenario, the test is based on a real-time PCR. Indeed, there exist several known in the art algorithms for extracting numerical features from real-time PCR amplification curves.

Further in the scenario, there exists a method for developing a model for classifying the real-time PCR amplification curves, provided the number of samples already labeled (i.e. classified into one of at least two classes) is sufficiently diverse for calibrating the model (i.e. for accurately defining the borders among different classes using the model).

However, in an early stage of the Zika outbreak, only a small number of the samples are classified in advance (say because only a small number of the people who live in the community show clinical symptoms specific to Zika or because of a shortage in Experts available for classifying the samples). Consequently, the number of samples that are already of labeled (i.e. classified into one of the at least two classes) is not sufficiently diverse for calibrating the model, as described in further detail hereinabove.

Reference is now made to FIG. 7, which is a first flowchart schematically illustrating an exemplary scenario of controlling the mixing of a plurality of samples subject to a chemical process, according to an exemplary embodiment of the present invention.

In order to overcome the problem of the insufficient diversity of labeled samples in the early stage of the first exemplary scenario, there is received 710 data on the results obtained using the real-time PCR process for all the samples, but for only a few of the samples is there received labeling data.

In the first scenario, each one of the received 710 results includes numerical features extracted from a real-time PCR amplification curve derived from fluorescence values measured during the real-time PCR process that a respective one of the samples is subject to, as described in further detail hereinabove.

Further in the scenario, at least one of the samples is known to be Positive and at least one of the samples is known to be Negative, thus at least two of the samples are received with classification data, as described in further detail hereinbelow.

Based on the received 710 results, there is performed a calibration 720, in which the classification model is enhanced, say through the methods described in further detail hereinabove and illustrated, for example, in FIG. 4.

Once calibrated 720, the classification model may be used 730 as a Classifier for any sample obtained later from the people in the faraway rural community, and potentially, for future Zika outbreaks that involve the new strand of the virus.

Reference is now made to FIG. 8, which is a second flowchart schematically illustrating the exemplary scenario of controlling the mixing of a plurality of samples subject to a chemical process, according to an exemplary embodiment of the present invention.

Thus, in the first scenario, there is received 810 data on the results obtained using the real-time PCR process for a few samples, at least one of which received 810 samples is known to be Positive and at least one of which received 810 samples is known to be Negative, as described in further detail hereinabove.

Using the known positive sample and known negative sample, there is prepared 820 a dilution series. In the preparation of the series, the negative sample is used as blank. Thus, in the first scenario, to yield the dilution series, the positive sample is diluted using the negative sample in predefined ratios (say in ratios of $1:10$, $1:10^2$, $1:10^3$, $1:10^4$ and $1:10^5$), as described in further detail hereinabove.

Each one the positive sample, negative sample, and the samples created when of the dilution series is prepared, is run through a real-time PCR process, and based on a result obtained using the process, a rank is calculated 830 for each respective one of the samples. The rank is calculated 830 by depicting the progress of the sample's PCR process in a real-time PCR amplification curve, and projecting the curve to a Fiedler Vector, as known in the art.

Then, the boundaries between different classes for which samples may be classified are found, in an attempt to calibrate a classification model, say through steps of the exemplary method illustrated using FIG. 4 hereinabove.

Then, the classification model is verified 850 against predefined criterion, say by verifying that none of the uncertainty regions that may be found among the samples when arranged according to their calculated 830 ranks exceed a user-defined maximal allowed difference, as described in further detail hereinabove.

If the classification model still fails to comply with the predefined criteria, there is synthesized 860 additional data.

The additional data may be synthesized 860 by obtaining classification data on a selected sample, or by mixing a pair of samples to yield one or more new samples likely be calculated a rank in between the ranks calculated for the samples in the pair, as described in further detail and illustrated using FIG. 4 hereinabove.

Then, after a number of iterations, the classification model complies with the predefined criteria, and the calibration of the classification ends 870 successfully, thus achieving a defined classifier. The defined classifier is thus a classification model in which the borders among different classes are judged to be accurately defined—say based on verifying that all gaps (i.e. uncertainty regions) that remain in the model are narrower than the user-defined maximal allowed difference, as described in further detail hereinabove.

Figure 9:
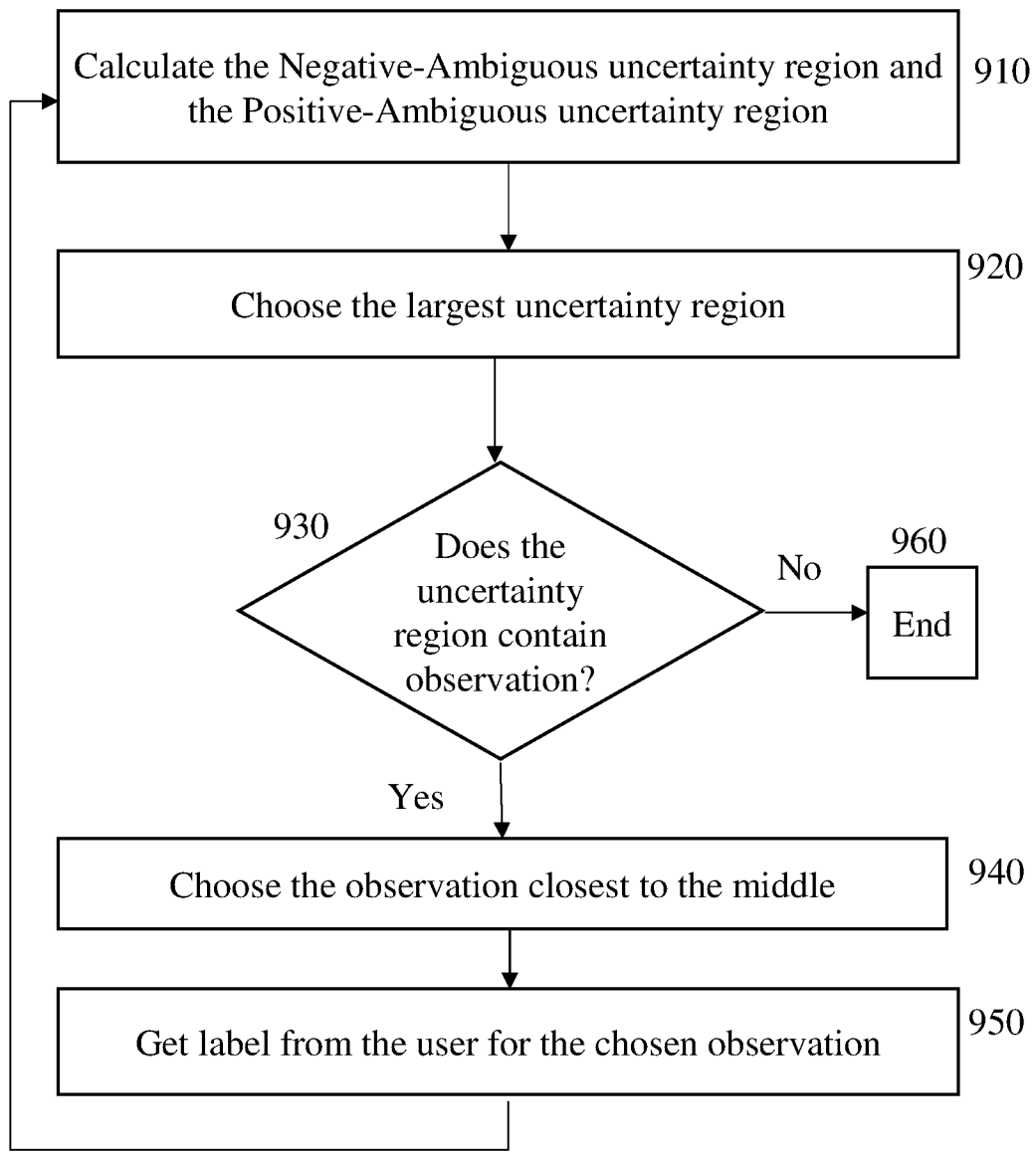
FIG. 9 is a third flowchart schematically illustrating the exemplary scenario of controlling the mixing of a plurality of samples subject to a chemical process, according to an exemplary embodiment of the present invention.

Reference is now made to FIG. 9, which is a third flowchart schematically illustrating the exemplary scenario of controlling the mixing of a plurality of samples subject to a chemical process, according to an exemplary embodiment of the present invention.

In the first exemplary scenario, the verifying 850 of the classification model against the predefined criteria includes identifying 910 a Negative-Ambiguous uncertainty region and a Positive-Ambiguous uncertainty region, as described in further detail hereinabove, and as illustrated for example, in FIG. 5C.

Then, there is found 920 the largest among the two uncertainty regions of the instant scenario, as described in further detail hereinabove.

In the scenario, there is checked 930 if the largest uncertainly region contains samples of a calculated rank in between the ranks calculated for the samples that define the region (say the ones at the edges of the region, as illustrated for example in FIG. 5C), for that verifying 850, as described in further detail hereinabove.

If the largest uncertainly region does contain samples of a rank in between the ranks calculated for the samples that define that region, there is found 940 among those samples, a sample with a rank closest to the average of the ranks calculated for the samples that define that region, as described in further detail hereinabove.

Then, there is obtained 950 a classification for the found 940 sample, as described in further detail hereinabove.

Following the obtaining 950 of the classification data for the found 940 sample, steps 910-930 are repeated over for that sample and the remaining samples.

Steps 910-940 may be iterated over until the largest uncertainty region remaining among the samples does not contain any sample 930, thus ending 960 a round of data obtaining 950 for samples within uncertainty regions.

However, the classification model may still fail to comply with the predefined criterion, say because there can still be found an uncertainly region defined by samples for which the difference between calculated ranks is greater than the user-defined maximal allowed difference (say the minimal resolution).

In one example, if the classification model fails to comply with the criterion, there are generated instructions for mixing one or more pairs of samples qualitatively identical to the pair of samples that define the uncertainty region, to yield one or more new samples, as described in further detail hereinabove.

In the example, subsequently to the mixing, each one of the new samples undergoes the chemical process, and data on a result obtained for the respective sample subject to the chemical process is received, say by the data receiver 110, as described in further detail hereinabove.

Then, new ranks are calculated for all samples for which data on the results is received, and steps 910-950 are iterated over again, until 960 no remaining uncertainty region is larger than the user-defined maximal allowed difference, as described in further detail hereinabove.

In the first exemplary scenario, there is thus learned the range of ranks which correspond to a responsive amplification curves, the range of ranks which correspond to non-responsive amplification curves, and the range of rank which corresponds to ambiguous amplification curves. Accordingly, in the scenario, the ranges correspond to a class of positive samples, a class of negative samples, and a class of ambiguous samples, respectively.

More specifically, the steps of the scenario may be carried out, for example, according to the method described in further detail hereinabove and illustrated using FIG. 4, say using the "Data Scanning procedure", as described in further detail hereinbelow.

In the scenario, in an early stage of the Zika outbreak, only a small number of the samples for which the data on the results is received are classified in advance.

At a first stage, only the ranks of the amplification curve generated for the negative sample and the rank of the amplification curve generated for the positive sample are generated. However, no information about the partition of the range of ranks into classes is known.

Optionally, in the scenario, uncertainty regions are found using the "Searching uncertainty regions procedure", as described in further detail hereinbelow.

In the scenario, in order to narrow down the uncertainty ranges (i.e. the gaps in the evolving classification model of the scenario), a user (say the PCR Expert) is asked to classify a sample having a rank that is closet to the mean of the ranks calculated for the pair of classified samples that defines that uncertainty region. The sample on which the user is asked may be selected for example, using the "Acquire observation from region procedure", as described in further detail hereinbelow.

After the user responds by providing classification data on the sample that the point nearest to the average represents, the partition of the range of rank values to classes is re-calculated.

In one example, if the user classified the sample as Positive, any sample with a calculated rank higher than that of the sample that the user classifies as Positive, is deemed responsive and is accordingly classified as Positive. However, it is still unclear how samples with a calculated rank lower than the sample that the user classifies as Positive are to be classified.

However, as the user is iteratively asked to classify more samples (say using their PCR amplification curves), the uncertainty regions are recalculated, and become narrower and narrower, as described in further detail hereinabove.

In one example, after three iterations one of the remaining uncertainty regions does not contain any sample, but is still larger than the predefined threshold (say the predefined minimal resolution), as described in further detail hereinabove.

In the example, in order to narrow further the uncertainty ranges, instructions for mixing are generated and forwarded to a machine (say a pipetting robot), as described in further detail hereinabove. The instructions may be generated for example using the "synthesize new observation procedure", as described in further detail hereinbelow.

In the example, each of the new samples created by the robot is subject to a real-time PCR, and to classification by the user, based on an amplification curve calculated based on the PCR process carried out on the sample.

Then, iteratively, new samples are created, respective amplification curves are generated, the user is asked to classify the samples using the curves, and uncertainty regions are recalculated.

After a number of iterations, the stop criteria procedure indicates that the largest uncertainty region left is narrower than a threshold (say the user-defined maximal allowed difference), the model is deemed calibrated. At this point, the classification model may be used to rank and classify future samples based on results carried obtained for future samples using a real-time PCR process.

Thus, in the exemplary scenario, there is defined a measurable ordering of the samples, based on the respective PCR reaction curves. Specifically, the samples are ordered along a range of rank values that spans a Negative (say non-responsive) part, an Ambiguous part, and a Positive (say responsive) part.

More specifically, in the exemplary scenario, for each one of the samples for which there is received respective data on the result obtained for the sample, there is calculated a respective rank based on the Fiedler Vector value calculated for the sample, as described in further detail hereinabove.

In the scenario, there is found a part of the range of Fiedler Vector values that corresponds to responsive and hence positive curves, a part of the range of Fiedler Vector values that corresponds to non-responsive and hence negative curves, and a part of the range of Fiedler Vector values that corresponds to ambiguous curves and is situated between the other two parts.

In the instant scenario, the method illustrated hereinabove using FIG. 4 may be implemented using the specific procedures detailed hereinbelow.

Synthesize New Observation Procedure

Input: A group of partially labeled points 'T', uncertainty region R.
1. Sort the points in T by the Fiedler Vector value.
2. Select the highest point in T which is lower than R, and call it lower point.
3. Select the lowest point in T which is higher than R, and call it higher point.
4. Order the machine (say robot) to mix the sample associated with the lower point with the sample associated with the higher point.
5. Obtain and return results of the PCR process and classification for the samples created by the mixing.

Acquire Observation from Region Procedure

Input: A group of partially labeled points 'T', uncertainty region R.
1. Create a subset S of T which contains only the points inside of R.
2. If S is empty, call the synthesize new observation procedure with the parameters T and R, return the point returned from the procedure, and finish this procedure.
3. Select the observation in S that is closest to the middle of R.
4. Return the selected observation.

Stop Criteria Procedure

Input: Uncertainty region and a group of partially labeled points 'T'.
1. Inspect the two points at the ends of the uncertainty region.
2. Get a dilution ratio for the two points.
3. If the dilution ratio is smaller than the machine's resolution or the PCR reaction's (say qPCR's) quantification resolution return 'true', else return 'false'.

Searching Uncertainty Regions Procedure

Input: A group of partially labeled points, with labels 'positive', 'negative', 'ambiguous'
1. Create a subset S which contains only the labeled points.
2. Sort S by the value of the Fiedler Vector value.
3. Iterate on S from the lowest calculated Fiedler Vector value to the highest calculated Fiedler Vector value.
4. If the first point is not labeled as negative, raise exception
5. While the selected point is labeled as negative, continue the iteration.
6. Choose the last point which is labeled as negative to be the start of the negative-ambiguous uncertainty region.
7. Choose the point after the start of the negative-ambiguous uncertainty region to be the end of the negative-ambiguous uncertainty region.
8. Iterate on S from the highest calculated Fiedler Vector value to the lowest calculated Fiedler Vector value.
9. If the first point is not labeled as positive, raise exception
10. While the selected point is labeled as positive, continue the iteration.
11. Choose the last point which is labeled as positive to be the end of the positive-ambiguous uncertainty region.
12. Choose the point after the end of the positive-ambiguous uncertainty region to be the start of the positive-ambiguous uncertainty region.
13. Return the negative-ambiguous uncertainty region and positive-ambiguous uncertainty region with the points that define the uncertainty regions.

Add Label to Observation Procedure

Variant A—Human expert

Input: An observation (i.e. a result obtained for one of the sample) denoted 'O'
1. A human expert is asked to examine a curve that depicts the progress of the PCR process for the sample, and give a label, say using a GUI (Graphical User Interface), thus classifying the sample as 'positive', 'negative' or 'ambiguous'
2. Return the label (i.e. classification of the sample) given by the human expert.

Variant B—Heuristics

Input: An observation (i.e. a result obtained for one of the sample) denoted 'O'.
1. one or more type of heuristics is used to classify to the observation, such as:
   a. an SNR—a measure of the ratio between the signal power and the signal standard deviation. For example, a chromatographic peak SNR can be calculated by taking the maximum intensity of the signal minus the baseline, divided by the standard deviation of the signal. A high SNR value is attributed to positive observation.
   b. Ct Range—Given a range of possible PCR efficiency and initial concentration, a positive observation will have Ct value in a certain range.
   c. RFU Threshold measured by taking the maximum signal and subtracting the baseline. RFU above a certain threshold is attributed to positive observation.
2. Return the label Variant C—Using LOD with Ambiguous Input: An observation 'O', the dilution ratio of the observation 'R', the initial specimen quantity 'Q', Limit Of Detection 'LOD'
1. Using R and Q, the quantity of the observation is determined.
2. The label is decided by the observation quantity and the LOD:
   a. If the observation quantity is above the LOD then the label is positive
   b. If the observation quantity is below the LOD and above zero concentration then the label is ambiguous
   c. If the observation quantity is equal to zero concentration then the label is negative
3. Return the label Variant D—Using LOD without ambiguous Input: An observation 'O', the dilution ratio of the observation 'R', the initial specimen quantity 'Q', Limit Of Detection 'LOD'
4. Using R and Q, the quantity of the observation is determined.
5. The label is decided by the observation quantity and the LOD
   a. If the observation quantity is above the LOD then the label is positive b. If the observation quantity is below the LOD then the label is negative
6. Return the label Data Scanning Procedure Input: A group of partially labeled points 'T'—each point representing a result of a respective one of the samples, with labels 'positive', 'negative', 'ambiguous'
1. Calculate negative-ambiguous uncertainty region and positive-ambiguous uncertainty region using Searching uncertainty regions procedure.
2. Select the largest uncertainty region.
3. Call stop criteria procedure with the largest uncertainty region and T.
4. If the stop criteria procedure returned true, finish this procedure.
5. Acquire new observation using the acquire observation from region procedure, with the parameters T and the selected uncertainty region.
6. Label to the acquired observation using the "Add label to observation procedure".
7. Add the acquired now labeled observation to T.
8. Goto line 1

It is expected that during the life of this patent many relevant devices and systems will be developed and the scope of the terms herein, particularly of the terms "Computer", "Processor", "Chip", "Robot", "PCR", and "HPLC" is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for controlling the mixing of a plurality of samples subject to a chemical process, the method comprising computer executed steps, the steps comprising:
   a) for each one of the samples, receiving respective data on a result obtained for the sample using the chemical process, and for each one of at least two of the samples, further receiving respective data on classification of the sample into one of at least two classes;
   b) for each one of the samples, calculating a respective rank based on the result obtained for the sample using the chemical process;
   c) finding among the samples, at least one pair of samples classified into different ones of the classes, such that for each respective one of the found pairs, none of the samples having a calculated rank lower than the calculated rank of a first one of the samples of the found pair and higher than the calculated rank of a second one of the samples of the found pair, are classified into one of the classes;
   d) identifying a pair consisting of samples that are least close to each other in their calculated ranks among the found pairs; and
   e) generating instructions for mixing at least one pair of samples qualitatively identical to the identified pair, to yield a respective new sample, said generating being conditioned upon none of the samples having a calculated rank lower than the calculated rank of a first one of the samples of the identified pair and higher than the calculated rank of a second one of the samples of the pair identified through steps a)-d); and
   f) controlling a machine for mixing the at least one pair of samples qualitatively identical to the identified pair, using the generated instructions.

2. The method of claim 1, further comprising generating instructions for mixing at least two pairs of samples qualitatively identical to the identified pair, each pair of samples being mixed in a different ratio.

3. The method of claim 1, further comprising an additional step preceded by step d, the additional step comprising obtaining data on classification of a sample of a calculated rank closest to an average of the ranks calculated for the samples in the identified pair, and following said obtaining, performing again said steps b to d.

4. The method of claim 1, further comprising an additional step preceded by step d, the additional step comprising obtaining data on classification of a sample of a calculated rank closest to an average of the ranks calculated for the samples in the identified pair from a user, and following said obtaining, performing again said steps b to d.

5. The method of claim 1, further comprising an additional step preceded by step d, the additional step comprising retrieving data on classification of a sample of a calculated rank closest to an average of the ranks calculated for the samples in the identified pair from a database, and following said retrieving, performing again said steps b to d.

6. The method of claim 1, further comprising an additional step preceded by step d, the additional step comprising classifying a sample having a calculated rank closest to an average of the ranks calculated for the samples in the identified pair according to predefined heuristics, and following said classifying, performing again said steps b to d.

7. The method of claim 1, wherein said generating of the instructions for the mixing is further conditioned upon compliance with a predefined criterion.

8. The method of claim 1, wherein said generating of the instructions for the mixing is further conditioned upon compliance with a criterion predefined for the chemical process.

9. The method of claim 1, wherein said generating of the instructions for the mixing is further conditioned upon compliance with a criterion predefined for a machine to be used for the mixing of the samples.

10. The method of claim 1, further comprising a step of running the chemical process on the sample for obtaining the result.

11. The method of claim 1, further comprising a step of running a PCR (Polymerase Chain Reaction) process on the sample for obtaining the result.

12. The method of claim 1, further comprising a step of deriving the results from measurements carried out during the chemical process.

13. The method of claim 1, wherein said calculating of the rank is further based on a Fiedler Vector.

14. The method of claim 1, further comprises identifying a most significant parameter based on the received results, wherein said calculating of the ranks is further based on the identified most significant parameter.

15. Apparatus for controlling the mixing of a plurality of samples subject to a chemical process, comprising:
- a computer processor;
- a data receiver, implemented on the computer processor, configured to receive for each one of the samples, respective data on a result obtained for the sample using the chemical process, and for each one of at least two of the samples, to further receive respective data on classification of the sample into one of at least two classes;
- a rank calculator, in communication with said data receiver, configured to calculate for each one of the samples, a respective rank based at least on the result obtained for the sample using the chemical process;
- a pair finder, in communication with said rank calculator, configured to find among the samples, at least one pair of samples classified into different ones of the classes, such that for each respective one of the found pairs, none of the samples having a calculated rank lower than the calculated rank of a first one of the samples of the found pair and higher than the calculated rank of a second one of the samples of the found pair, are classified into one of the classes;
- a least close pair identifier, in communication with said pair finder, configured to identify a pair consisting of samples that are least close to each other in their calculated ranks among the found pairs; and
- an instruction generator, in communication with said least close pair identifier, configured to generate instructions for mixing at least one pair of samples qualitatively identical to the identified pair, to yield a respective new sample, said generating being conditioned upon none of the samples having a calculated rank lower than the calculated rank of a first one of the identified pair and higher than the calculated rank of a second one of the samples of the identified pair, and to control a machine for mixing the at least one pair of samples qualitatively identical to the identified pair, using the generated instructions.

16. The apparatus of claim 15, further comprising a reaction apparatus, in communication with said data receiver, configured to run the chemical process on the sample for obtaining the result, wherein said data receiver is adapted for receiving the data on the result obtained for the sample using the chemical process, from said reaction apparatus.

17. The apparatus of claim 15, further comprising a PCR machine, in communication with said data receiver, configured to run a PCR (Polymerase Chain Reaction) process on the sample for obtaining the result, wherein said data receiver is adapted for receiving the data on the result obtained for the sample using the chemical process, from said PCR machine.

18. The apparatus of claim 15, further comprising a result deriver, in communication with said data receiver, configured to derive the results from measurements carried out during the chemical process.

19. A non-transitory computer readable medium storing computer processor executable instructions for performing steps of controlling the mixing of a plurality of samples subject to a chemical process, the steps comprising:
- a) for each one of the samples, receiving respective data on a result obtained for the sample using the chemical process, and for each one of at least two of the samples, further receiving respective data on classification of the sample into one of at least two classes;
- b) for each one of the samples, calculating a respective rank based on the result obtained for the sample using the chemical process;
- c) finding among the samples, at least one pair of samples classified into different ones of the classes, such that for each respective one of the found pairs, none of the samples having a calculated rank lower than the calculated rank of a first one of the samples of the found pair and higher than the calculated rank of a second one of the samples of the found pair, are classified into one of the classes;
- d) identifying a pair consisting of samples that are least close to each other in their calculated ranks among the found pairs; and
- e) generating instructions for mixing at least one pair of samples qualitatively identical to the identified pair, to yield a respective new sample, said generating being conditioned upon none of the samples having a calculated rank lower than the calculated rank of a first one of the samples of the identified pair and higher than the calculated rank of a second one of the samples of the pair identified through steps a)-d), the at least one pair of samples being mixed being; and
- f) controlling a machine for mixing the at least one pair of samples qualitatively identical to the identified pair, using the generated instructions.

* * * * *